United States Patent
Goldfarb et al.

(10) Patent No.: US 8,652,218 B2
(45) Date of Patent: Feb. 18, 2014

(54) POWERED LEG PROSTHESIS AND CONTROL METHODOLOGIES FOR OBTAINING NEAR NORMAL GAIT

(75) Inventors: Michael Goldfarb, Franklin, TN (US); Huseyin Atakan Varol, Nashville, TN (US); Frank Charles Sup, IV, Nashville, TN (US); Jason Mitchell, Greenbrier, TN (US); Thomas J. Withrow, Brentwood, TN (US)

(73) Assignee: Vanderbilt University, Nashville, TN (US)

( * ) Notice: Subject to any disclaimer, the term of this patent is extended or adjusted under 35 U.S.C. 154(b) by 295 days.

(21) Appl. No.: 12/427,384

(22) Filed: Apr. 21, 2009

(65) Prior Publication Data

US 2009/0265018 A1    Oct. 22, 2009

Related U.S. Application Data

(60) Provisional application No. 61/046,684, filed on Apr. 21, 2008.

(51) Int. Cl.
*A61F 2/48* (2006.01)
*A61F 2/64* (2006.01)
*A61F 2/62* (2006.01)

(52) U.S. Cl.
USPC ............. 623/40; 623/39; 623/47; 623/24

(58) Field of Classification Search
USPC ............ 623/40, 47, 27, 39, 41–46, 48–52, 24
See application file for complete search history.

(56) References Cited

U.S. PATENT DOCUMENTS

| | | | |
|---|---|---|---|
| 5,246,465 A * | 9/1993 | Rincoe et al. | 623/39 |
| 7,153,242 B2 | 12/2006 | Goffer | |
| 7,628,766 B1 | 12/2009 | Kazerooni et al. | |
| 8,057,550 B2 | 11/2011 | Clausen et al. | |
| 2004/0039454 A1 | 2/2004 | Herr et al. | |
| 2004/0088057 A1 * | 5/2004 | Bedard | 623/25 |
| 2004/0111163 A1 * | 6/2004 | Bedard et al. | 623/33 |
| 2006/0173552 A1 * | 8/2006 | Roy | 623/24 |
| 2006/0184280 A1 * | 8/2006 | Oddsson et al. | 700/245 |
| 2006/0224247 A1 * | 10/2006 | Clausen et al. | 623/24 |
| 2006/0249315 A1 * | 11/2006 | Herr et al. | 180/8.1 |
| 2007/0043449 A1 * | 2/2007 | Herr et al. | 623/24 |
| 2009/0299489 A1 * | 12/2009 | Gramnaes | 623/27 |

OTHER PUBLICATIONS iWalk, In the News FAQ; Retrieved on Aug. 2, 2011 from http://iwalk.com/IntheNews/faq.html.

(Continued)

*Primary Examiner* — David Isabella
*Assistant Examiner* — Jacqueline Woznicki
(74) *Attorney, Agent, or Firm* — Novak Druce Connolly Bove + Quigg LLP; Eduardo J. Quinones

(57) ABSTRACT

A powered leg prosthesis includes powered knee joint comprising a knee joint and a knee motor unit for delivering power to the knee joint. The prosthesis also includes a prosthetic lower leg having a socket interface coupled to the knee joint and a powered ankle joint coupled to the lower leg opposite the knee joint comprising an ankle joint and an ankle motor unit to deliver power to the ankle joint. The prosthesis further includes a prosthetic foot coupled to the ankle joint, at least one sensor for measuring a real-time input, and at least one controller for controlling movement of the prosthesis based on the real-time input.

23 Claims, 19 Drawing Sheets

(56) References Cited

OTHER PUBLICATIONS

Prosthetics, Hydracadence Knee: Handicap Technologie; PROTEOR: Retrieved on Aug. 12, 2011 from http://orthopaedics.proteor.com/report,27-hydracadence-knee.php.

Power Knee, Instructions for Use; Copyright Ossur 2010.

Sup et al, "Design of a Pneumatically Actuated Transfemoral Prosthesis", IMECE2006-15707, ASME International Mechanical Engineering Congress and Exposition, Nov. 5-10, 2006 by ASME.

U.S. Non-Final Office Action dated Dec. 31, 2012, in corresponding U.S. Appl. No. 13/115,175.

* cited by examiner

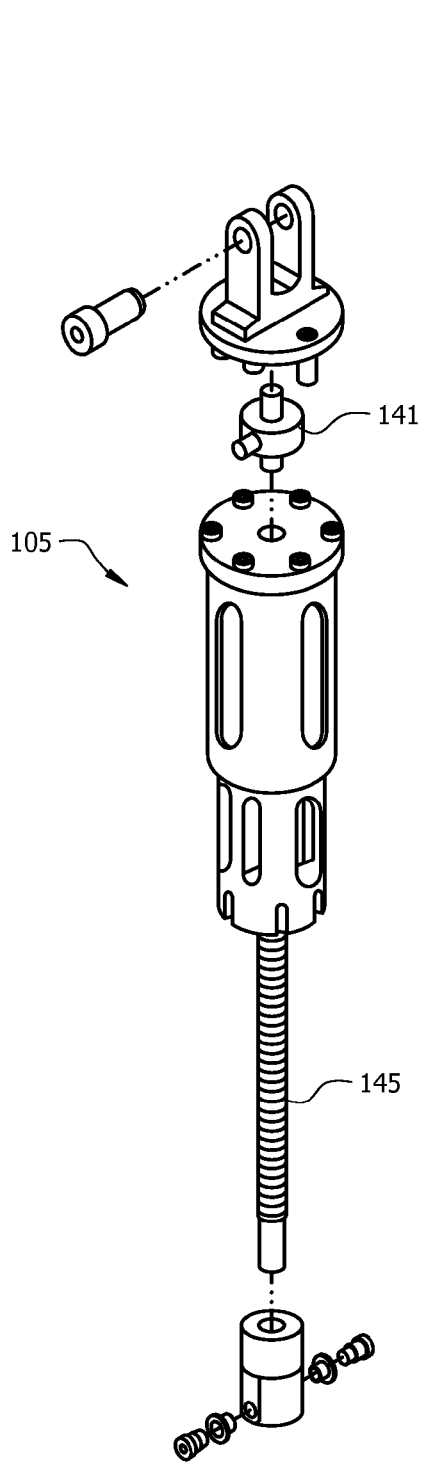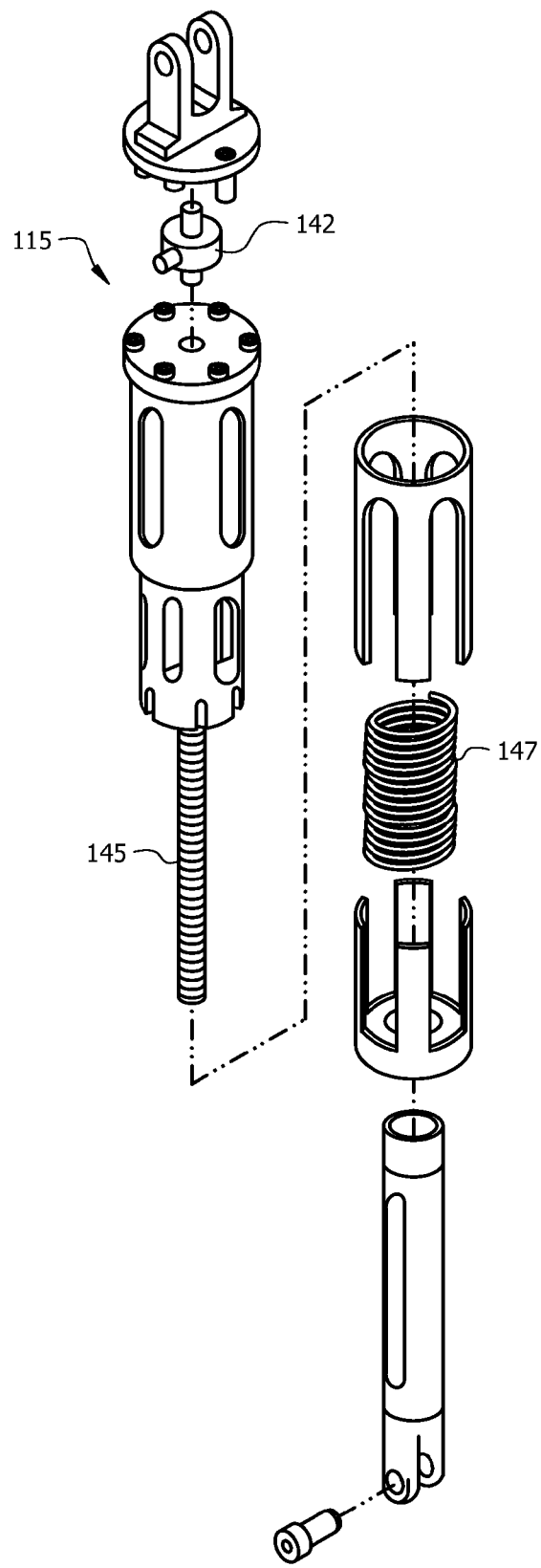
FIG. 2
FIG. 3

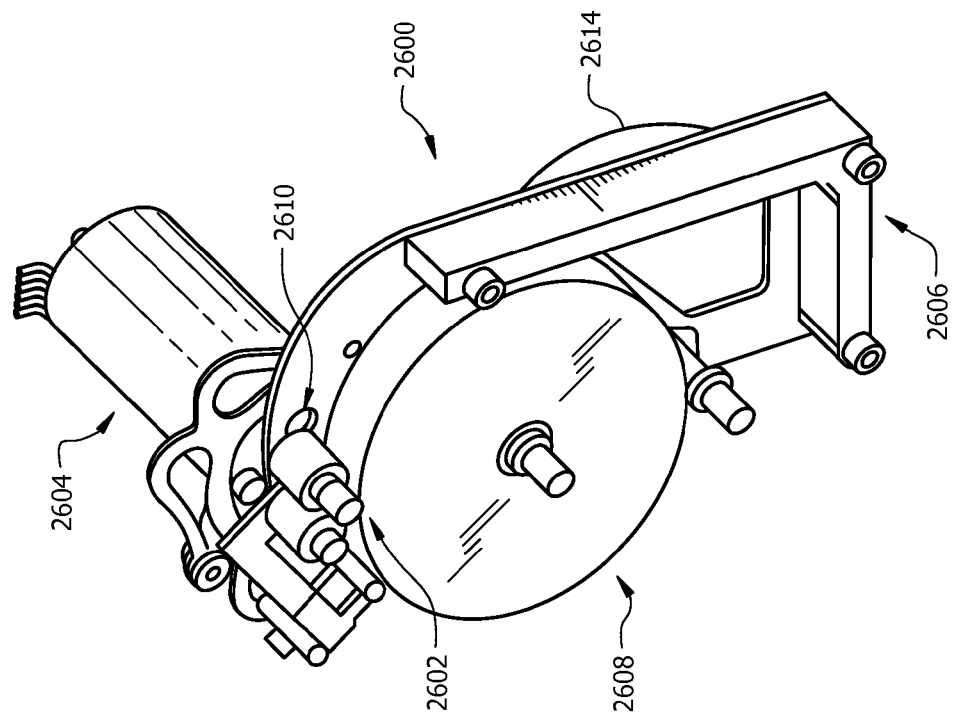
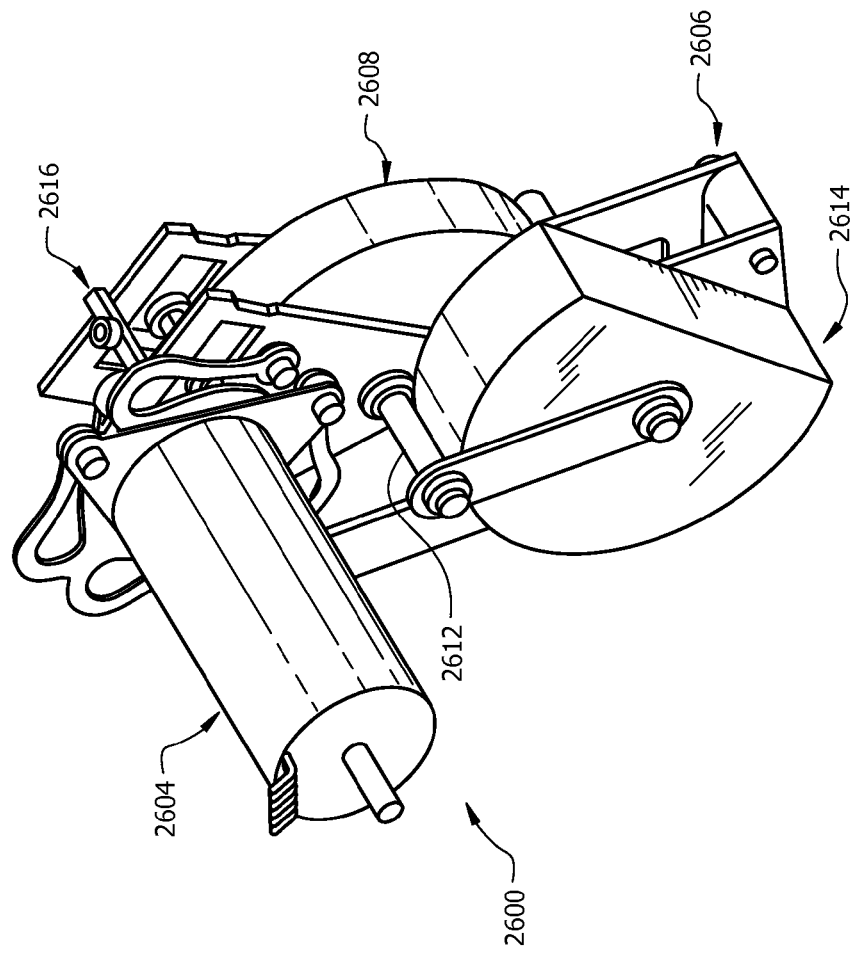
FIG. 26B
FIG. 26A

POWERED LEG PROSTHESIS AND CONTROL METHODOLOGIES FOR OBTAINING NEAR NORMAL GAIT

CROSS REFERENCE TO RELATED APPLICATIONS

This application claims the benefit of Provisional Application Ser. No. 61/046,684 entitled "POWERED LEG PROSTHESIS AND CONTROL METHODOLOGIES FOR OBTAINING NEAR NORMAL GAIT", filed Apr. 21, 2008, which is herein incorporated by reference in its entirety.

FEDERAL RIGHTS STATEMENT

The U.S. Government has certain rights to the invention based on National Institutes of Health Grant R01EB005684-01.

FIELD OF THE INVENTION

The invention relates to a powered leg prosthesis and control methodologies for controlling the prosthesis.

BACKGROUND

Leg prostheses can provide an artificial ankle, and artificial knee, or both an artificial ankle and an artificial knee. A transfemoral prosthesis is a prosthesis designed for above the knee amputees. Transfemoral prostheses are generally more complicated than transtibial prostheses, as they must include a knee joint.

Nearly all current commercial transfemoral comprising prostheses are energetically passive devices. That is, the joints of the prostheses either store or dissipate energy, but do not provide net power over a gait cycle. The inability to deliver joint power impairs the ability of these prostheses to restore many locomotive functions, including walking up stairs and up slopes. Moreover, there is a need for a leg prosthesis that provides a more natural gait behavior.

SUMMARY

This Summary is provided to comply with 37 C.F.R. §1.73, presenting a summary of the invention to briefly indicate the nature and substance of the invention. It is submitted with the understanding that it will not be used to interpret or limit the scope or meaning of the claims. Embodiments of the invention provide power leg prostheses and associated methods for control.

In a first embodiment of the invention, a powered leg prosthesis is provided. The prosthesis includes a powered knee joint comprising a knee joint and a knee motor unit for delivering power to the knee joint, a prosthetic lower leg having a socket interface above the knee joint, a powered ankle joint coupled to the lower leg opposite the knee joint comprising an ankle joint and an ankle motor unit to deliver power to the ankle joint, and a prosthetic foot coupled to the ankle joint. The prosthesis also includes at least one sensor for measuring a real-time input, and at least one controller for controlling movement of the prosthesis based on the real-time input.

In a second embodiment of the invention, a method is provided for controlling a powered leg prosthesis comprising at least one of an ankle and a knee joint, the leg prosthesis coupled to a user of the prosthesis. The method includes representing behavior of the at least one joint as a plurality of different activity modes, and within each activity mode a plurality of different internal phases, and responsive to sensing of at least one input initiated by the user, switching between the internal phases and activity modes. In the method, net energy can be delivered to the at least one joint upon the switching between the internal phases, and no net energy is delivered to the at least one joint if the internal phases remain unchanged.

In a third embodiment of the invention, a powered leg prosthesis is provided. The prosthesis includes a powered knee joint comprising a knee joint and a knee motor unit for delivering power to the knee joint, a prosthetic lower leg having a socket interface above the knee joint, a powered ankle joint coupled to the lower leg opposite the knee joint comprising an ankle joint and an ankle motor unit to deliver power to the ankle joint, and a prosthetic foot including a ball and a heel. The prosthesis also includes at least one sensor for providing a sagittal plane moment, and ground interaction forces at the ball and at the heel, and at least one controller coupled to the sensor for extracting real-time input from the user based on data from the sensor for controlling movement of the prosthesis.

BRIEF DESCRIPTION OF THE DRAWINGS

FIG. 2 is an exploded view of knee motor unit, according to an embodiment of the invention.

FIG. 3 is an exploded view of ankle motor unit, according to an embodiment of the invention

FIGS. 26A and 26B show front and back views of a friction/cable drive motor in accordance with an embodiment of the invention.

DETAILED DESCRIPTION

Figure 1A:
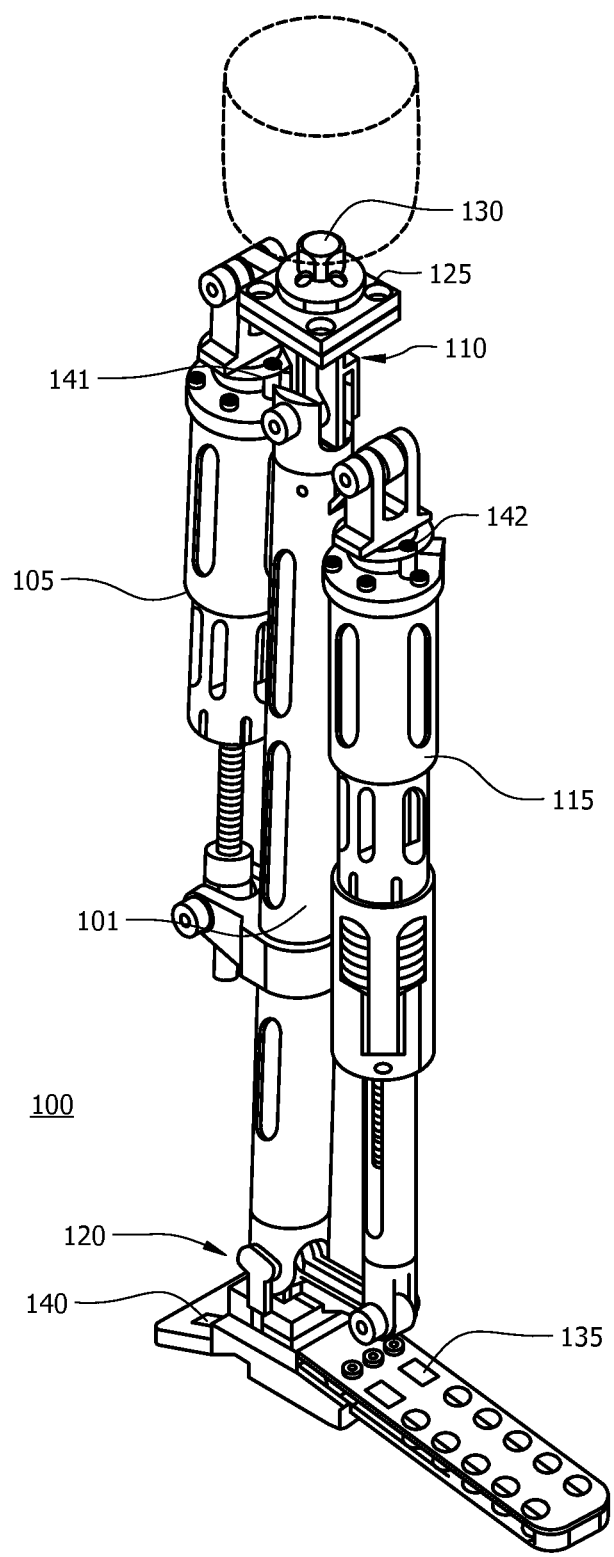
FIG. 1A is a view of a powered knee and ankle prosthesis, according to an embodiment of the invention.

The invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention. The invention is not limited by the illustrated ordering of acts or events, as some acts may occur in different orders and/or concurrently with other acts or events. Furthermore, not all illustrated acts or events are required to implement a methodology in accordance with the invention.

The present inventors have observed that biomechanically normal walking requires positive power output at the knee joint and significant net positive power output at the ankle joint. Embodiments of the invention provide a prosthesis that delivers power at both the knee and ankle joints. Unlike prior disclosed leg prosthetics that generate a desired joint trajectory for the prosthetic leg based on measurement of the sound leg trajectory and thus requires instrumentation of the sound leg, embodiments of the invention do not generally require instrumentation of the sound leg. Prostheses including transfemoral prostheses according to embodiments of the invention generally provide power generation capabilities comparable to an actual limb and a gait-based control framework for generating the required joint torques for locomotion while ensuring stable and coordinated interaction with the user and the environment. Embodiments of the invention thus enable the restoration of substantially biomechanically normal locomotion.

One design for a prosthesis according to an embodiment of the invention is shown in FIG. 1A through FIG. 6B. The prosthesis 100 comprises a prosthetic lower leg 101. Lower leg 101 can be coupled to a powered knee joint comprising a knee motor unit 105 coupled to a knee joint 110, and a powered ankle joint comprising an ankle motor 115 coupled to an ankle joint 120. A sagittal plane moment sensor 125 can be located between the prosthesis and the user to measure the moment, and in one embodiment is located immediately below the socket interface 130. In the embodiment shown, sensor 125 measures the sagittal plane moment, while separate sensors described below measure the ball of foot force and heel force with respect to the ground or other object the foot is pressed against. A load sensor 135 can be positioned at the ball of the foot, and a load sensor 140 can be positioned at the heel of the foot. However, in another embodiment (not shown) sensor 125 can measure the sagittal plane moment, the frontal plane moment and the axial force, such as provided by the three-axis socket load cell. This alternate embodiment can eliminate the need for sensor 135 and sensor 140.

Figure 4:
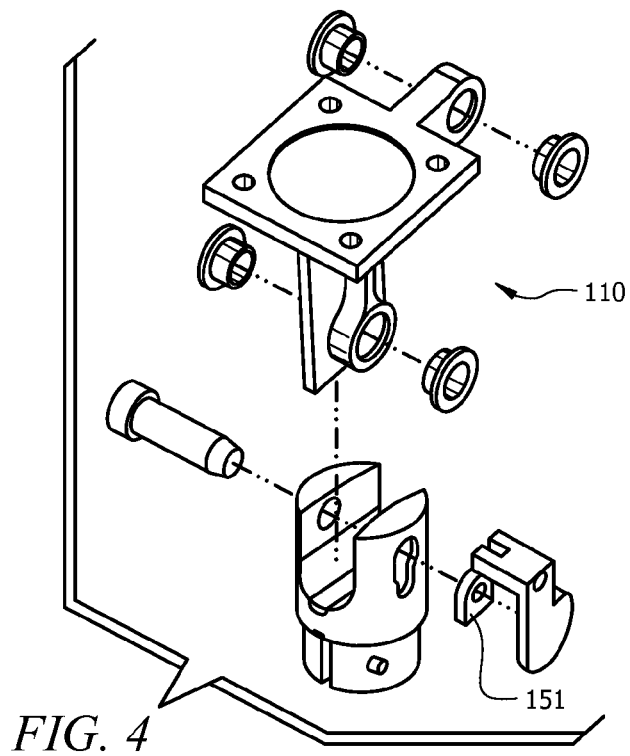
FIG. 4 is an exploded view of knee joint, according to an embodiment of the invention.
Figure 5:
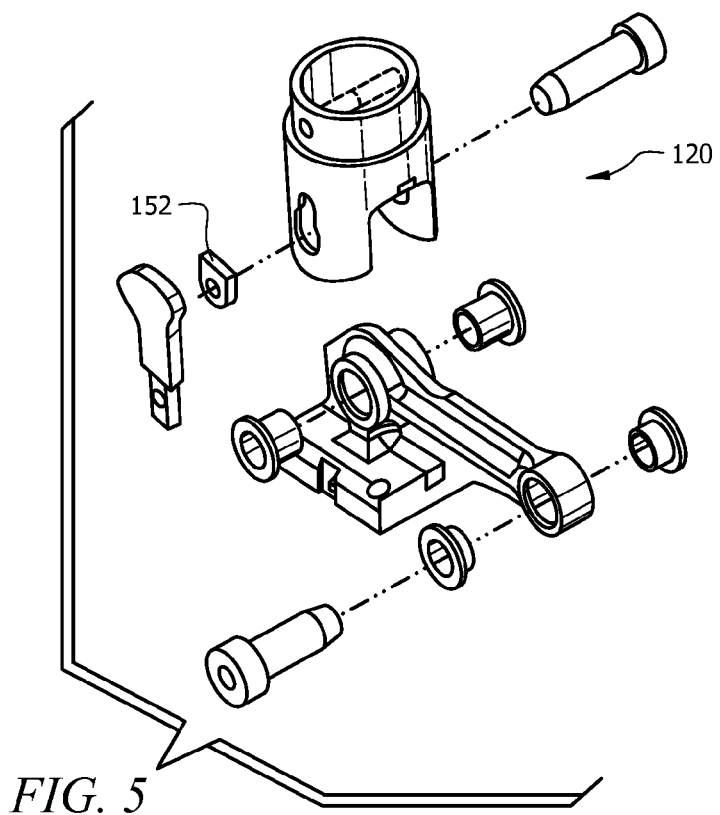
FIG. 5 is an exploded view of ankle joint, according to an embodiment of the invention.

Load sensors 141 and 142 are in series with each motor unit 105 and 115, respectively for motor unit force control. Position sensors 151 and 152 are provided at each joint 110 and 120 as shown in FIGS. 4 and 5 respectively. Position sensors 151 measure joint angle (θ as used below) and can be embodied as potentiometers. The computer/process controller, and power source (e.g. a battery such as a Li ion battery, and electrical connections in the case of an electrical power source are not shown to avoid obscuring aspects of the invention. Non-electrical power sources may also be used, such as pneumatic power, or non-battery electrical sources, such as hydrogen-based fuel cells.

Figure 1B:
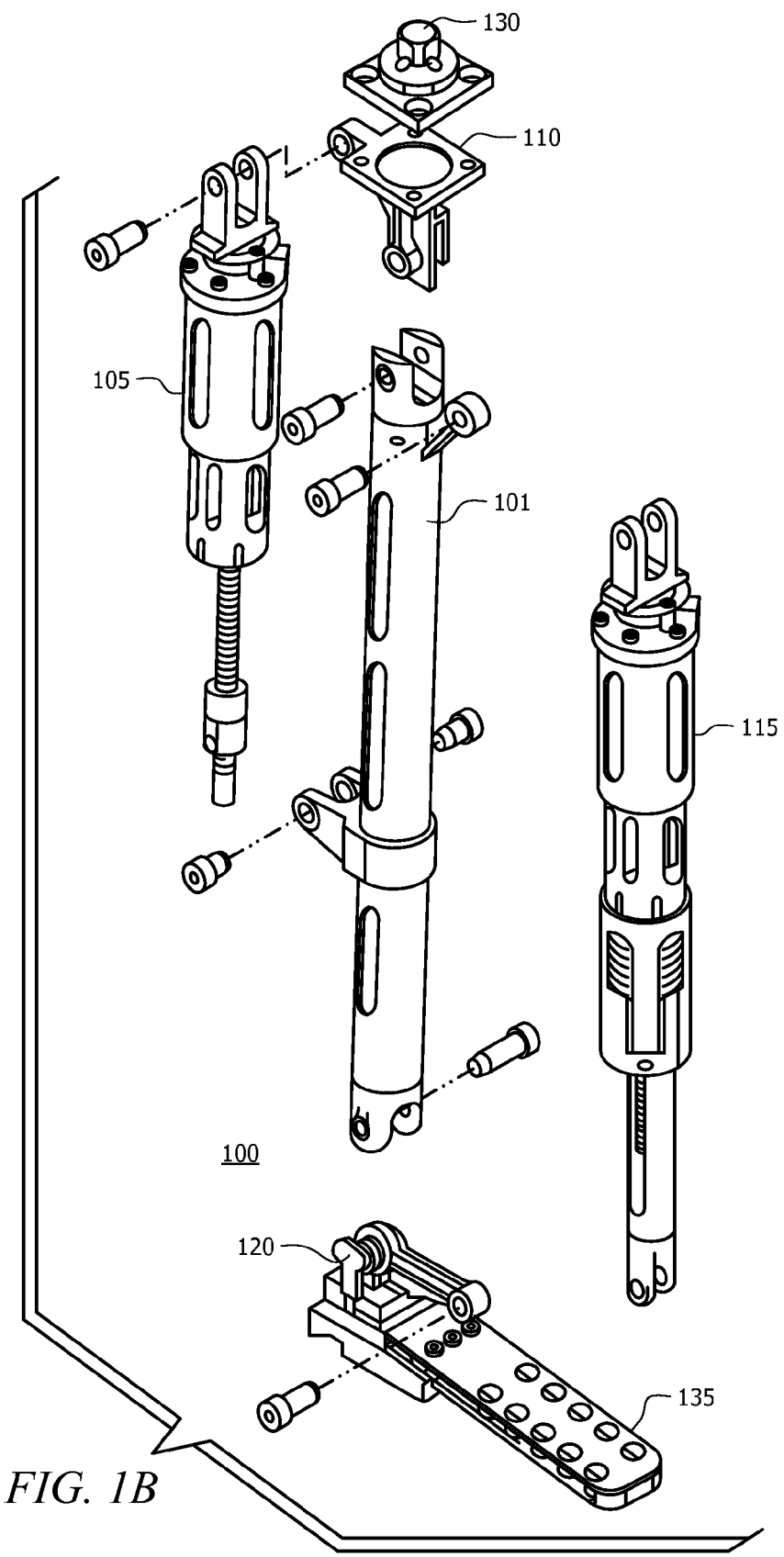
FIG. 1B is an exploded view of the powered knee and ankle prosthesis shown in FIG. 1A, according to an embodiment of the invention.

Prosthesis 100 is shown in an exploded view in FIG. 1B. Joints 110 and 120 are more clearly shown as compared to FIG. 1A.

FIG. 2 is an exploded view of knee motor unit 105, according to an embodiment of the invention. Load sensor 141 is shown as a load cell (e.g. strain gauge). Load sensor 141 measures force and moments. The motor unit 105 comprises a motor-driven ball screw assembly which drives the knee joint through a slider-crank linkage comprising screw 145. Other motor drive assemblies may also generally be used.

FIG. 3 is an exploded view of ankle motor unit 115, according to an embodiment of the invention. Load sensor 142 is generally analogous to load sensor 141. The motor unit 115 comprises a motor-driven ball screw assembly which drives the ankle joint through a slider-crank linkage comprising screw 145. The ankle motor 115 includes a spring 147 positioned to provide power in parallel (thus being additive) with power provided by the motor unit 115. Spring 147 biases the motor unit's force output toward ankle plantarflexion, and supplements the power output provided by motor unit 115 during ankle push off.

FIG. 4 is an exploded view of knee joint 110, according to an embodiment of the invention. As described above, knee joint 110 includes position sensor 151 that can be embodied as a potentiometer for angle measurements of the knee joint 110.

FIG. 5 is an exploded view of ankle joint 120, according to an embodiment of the invention. As described above, ankle joint 120 includes position sensor 152 that can be embodied as a potentiometer for angle measurements of the ankle joint 120.

Figure 6A:
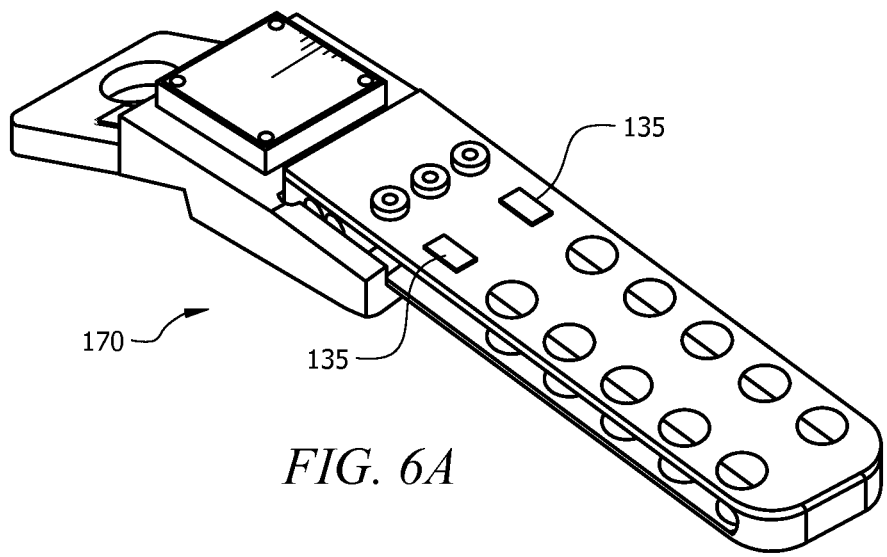
FIGS. 6A and B are views of a foot having toe and heel force sensing elements, according to an embodiment of the invention.
Figure 6B:
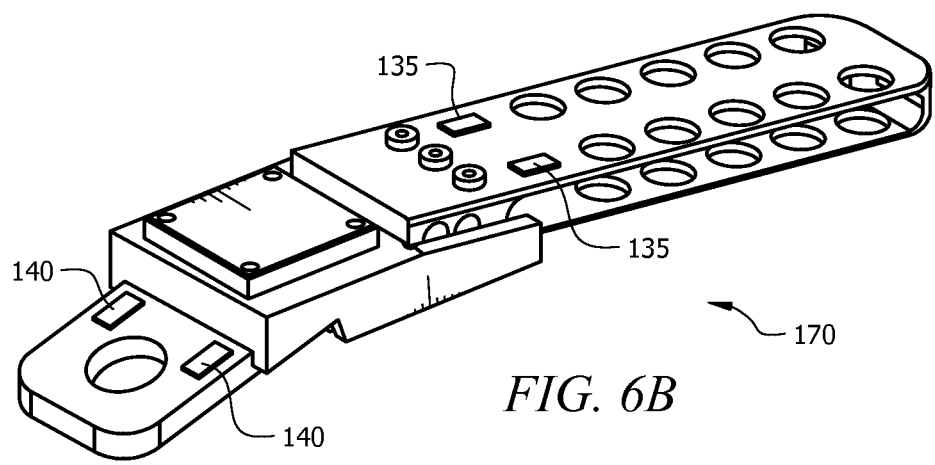

FIG. 6A is a view of a foot 170 having ball of foot sensors 135, according to an embodiment of the invention. Sensors 135 are provided to measure the ground reaction forces near the ball of the foot, such as when the foot strikes the ground. FIG. 6B is a view of a foot 170 having ball of foot sensors 135 and heel sensors 140, according to an embodiment of the invention. Sensors 140 are provided to measure the ground reaction forces on the heel of the foot when the foot 170 strikes the ground. Sensors 135 and 140 can be embodied as strain based sensors.

As described above, prostheses according to embodiments of the invention generally provide a gait-based control framework for generating the required joint torques for locomotion while ensuring stable and coordinated interaction with the user and the environment. This enables embodiments of the invention to restore substantially biomechanically normal locomotion.

Regarding control of the prosthesis, conventional prosthetic control schemes utilize position-based control which comprises generation of a desired joint angle/position trajectories, which by its nature, must utilize the prosthesis itself as a position source (e.g. "echo-control" based approaches). Such an approach poses several problems for the control of a powered prosthesis, such as prostheses according to embodiments of the invention. First, the desired position trajectories are typically computed based on measurement of the sound side (normal) leg trajectory, which 1) is not well suited to bilateral amputees, 2) requires instrumentation of the sound side leg, and 3) generally produces an even number of steps, which can present a problem when the user desires an odd number of steps. A subtle yet significant issue with conventional position-based control is that suitable motion tracking requires a high output impedance (i.e., joints must be stiff), which forces the amputee to react to the limb rather than interact with or more generally control the prosthetic limb. Specifically, in order for the known prosthesis to dictate the joint trajectory, it must generally assume a high output impedance, thus substantially precluding dynamic interaction with the user and the environment.

Unlike existing passive prostheses, the introduction of power into a prosthesis according to embodiments of the invention provides the ability for the device to also act, rather than simply react. As such, the development of a suitable controller and control methodology that provides for stable and reliable interaction between the user and prosthesis is provided herein. Control according to embodiments of the invention has been found to enable the user to interact with the prosthesis by leveraging its dynamics in a manner similar to normal gait, and also generates more stable and more predictable behavior.

Thus, rather than gather user intent from the joint angle measurements from the contralateral unaffected leg, embodiments of the invention infer commands from the user via the (ipsilateral) forces and moments of interaction between the user and prosthesis. Specifically, the user interacts with the prosthesis by imparting forces and moments from the residual limb to the prosthesis, all of which can be measured via suitable sensor(s), such as sensors 125, 140 and 141 described above which measures moments/forces. These forces and moments serve not only as a means of physical interaction, but also serve as an implicit communication channel between the user and device, with the user's intent encoded in the measurements. Inferring the user's intent from the measured forces and moments of interaction according to embodiments of the invention provides several advantages relative to the known echo approach.

In one embodiment of the invention the torque required at each joint during a single stride (i.e. a single period of gait) can be piecewise represented by a series of passive impedance functions. A regression analysis of gait data indicates that joint torques can be characterized by functions of joint angle ($\theta$) and angular velocity by an impedance model, such as the following exemplary passive impedance function shown in equation 1 below:

$$\tau = k_1(\theta - \theta_e) + b*\dot{\theta} \qquad (1)$$

where $k_1$, b, and the equilibrium joint angle $\theta_e$ are all constants that are generally generated empirically, and are constants for a given joint during a given internal phase (e.g. knee, internal phase 3). $k_1$ characterizes the linear stiffness. b is the linear damping coefficient, $\theta$ is the measured joint angle which can characterize the state of the prosthesis, $\theta_e$ is the equilibrium angle, $\dot{\theta}$ is the angular velocity of the joint, and $\tau$ is the joint torque. Given these constants, together with instantaneous sensor measurements for $\theta$ and $\dot{\theta}$, the torque ($\tau$) at the joints (knee and ankle) can be determined.

Figure 7:
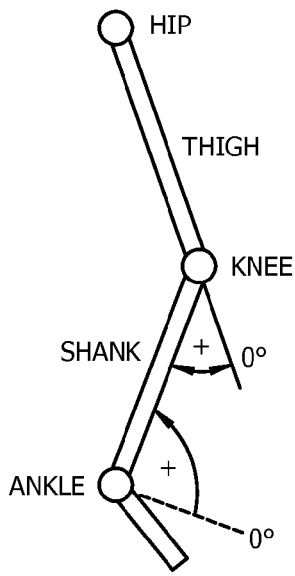
FIG. 7 shows the joint angle and torque convention used herein. Positive torque is defined in the direction of increasing angle.

Positive directions of the angle ($\theta$) and torque ($\tau$) as used herein are defined as shown in FIG. 7. If the coefficients b and $k_1$ are constrained to be positive, then the joints will each exponentially converge to a stable equilibrium at $\theta = \theta_e$ and $\dot{\theta} = 0$ within each internal phase. That is, within any given internal phase, the actuators are energetically passive (i.e. the joint will come to rest at a local equilibrium). While the unactuated prosthesis can be energetically passive, the behavior of one joint (knee or ankle) or the combined behavior of the knee and ankle joints, can be likewise passive, and thus will generally respond in a predictable manner.

Responsive to direct input from the user (e.g. a heel strike) to trigger a change in internal phase, power (torque) can be delivered from the power source (e.g. battery) to the prosthesis in the proper magnitude to provide the desired movement. Since the switching can be triggered by direct input from the user related to the current internal phase, the user maintains direct influence over the power applied to the prosthesis. If the user does not trigger the next internal phase (i.e. remains stationary) no net energy is delivered. That is, the prosthesis will generally cease to receive power from the power source for moving the joint, and will instead, due to the damped response, soon come to rest at the local equilibrium identified with the present internal phase.

As described above, the decomposition of joint behavior into passive segments requires the division of the gait cycle into a plurality of internal phases or "finite states" characterized by an impedance function and a set of constants for the impedance function, as dictated by their functions and the character of the piecewise segments of the impedance functions described above. The switching rules between internal phases should generally be well defined and measurable, and the number of phases should be sufficient to provide a substantially accurate representation of normal joint function. In one embodiment of the invention, the swing and stance phase of gait can constitute a minimal set of internal phases.

Figure 8:
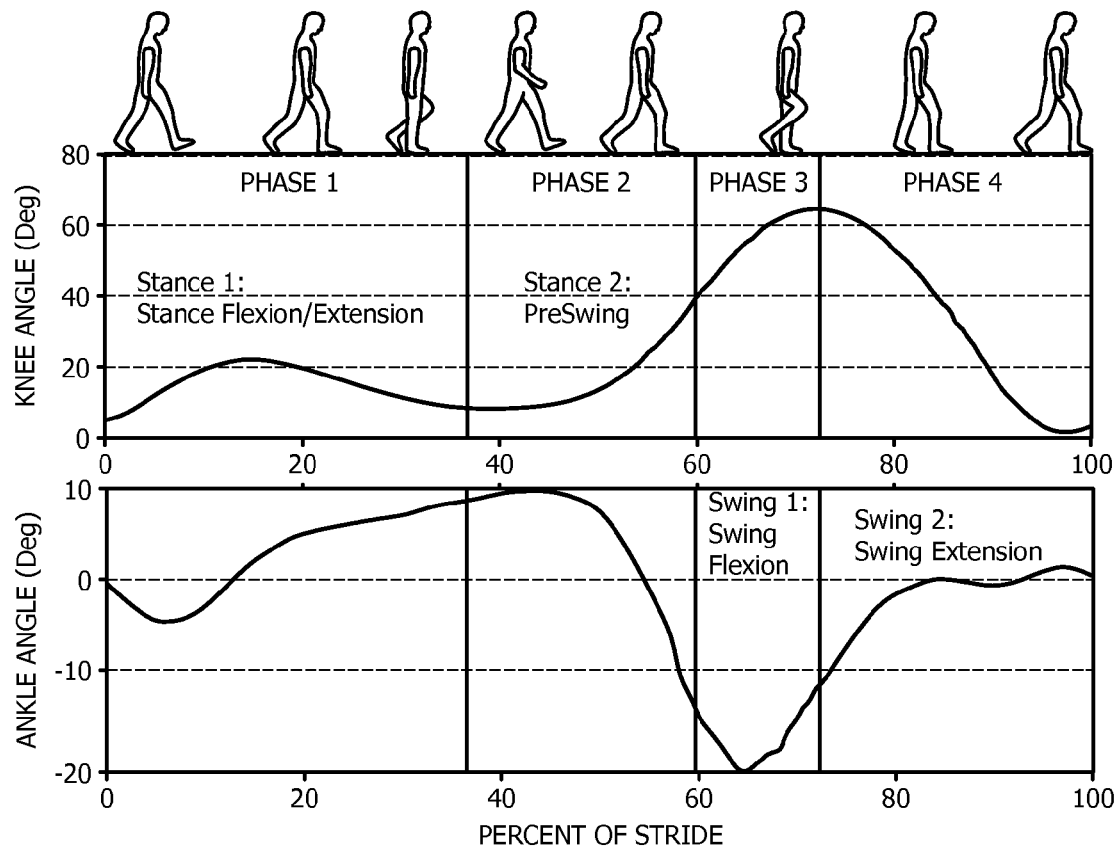
FIG. 8 shows the subdivision of normal walking into four internal phases showing the knee and ankle angles during the phases, according to an embodiment of the invention.
Figure 16:
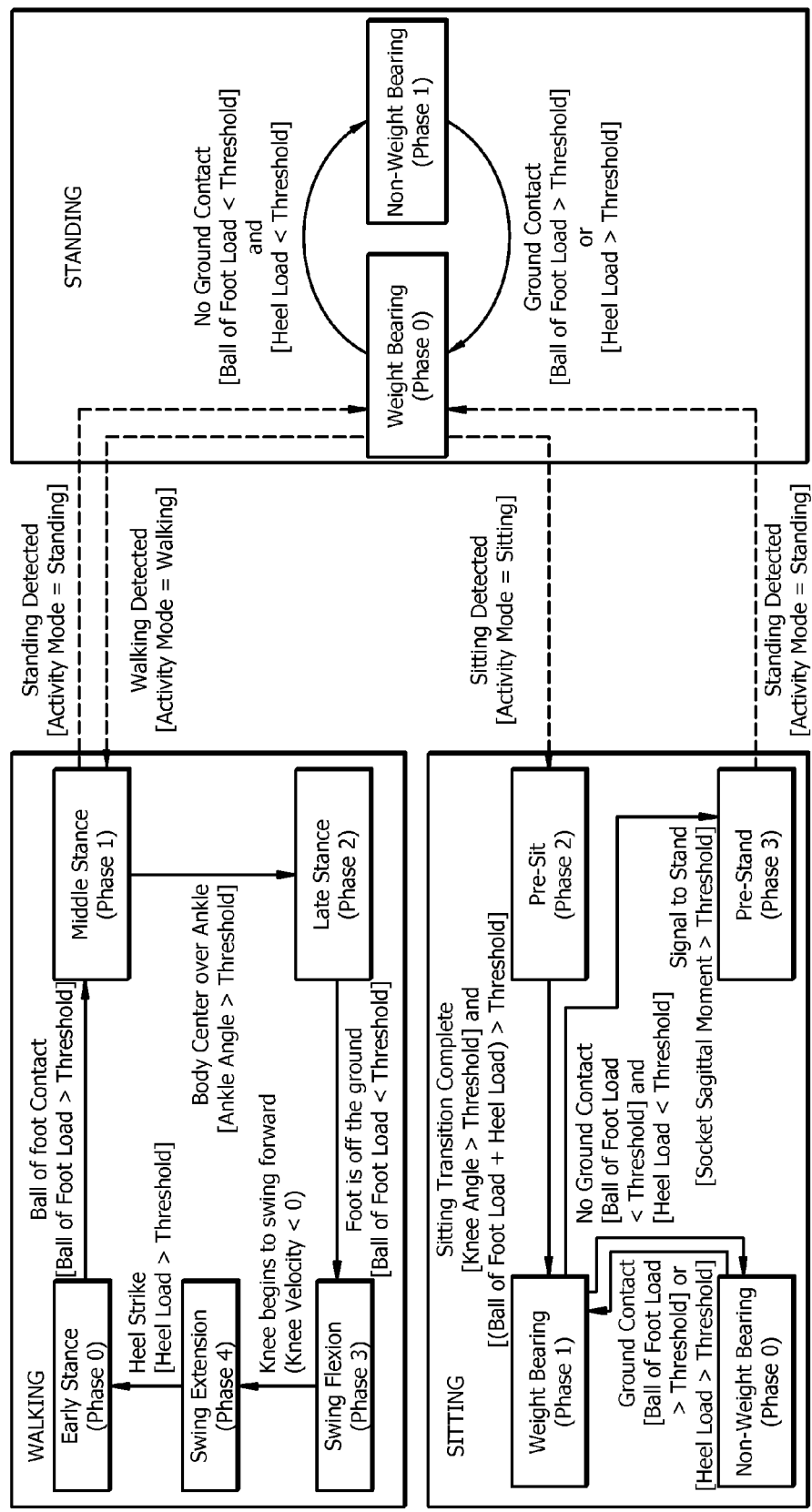
FIG. 16 is a control state chart for the three activity modes corresponding to walking, standing, and sitting, and for the internal phases and their corresponding transitions within each activity mode.

Based on least-squares regression fitting of Equation 1 to empirical gait data, the present Inventors determined that such fits were improved significantly by further dividing the two modes of swing and stance each into two additional internal phases to realize four phases, as shown in FIG. 8. A fifth internal phase can also be added, as illustrated in FIG. 16. The angle ($\theta$) of the prosthetic knee (above) and ankle joint (below) can be provided during each internal phase as a function of the % of the stride. Angle values shown can be used as threshold values to trigger phase changes as described below relative to FIG. 9. As clear to one having ordinary skill in the art, the number of phases can be other than two or four.

Figure 9:
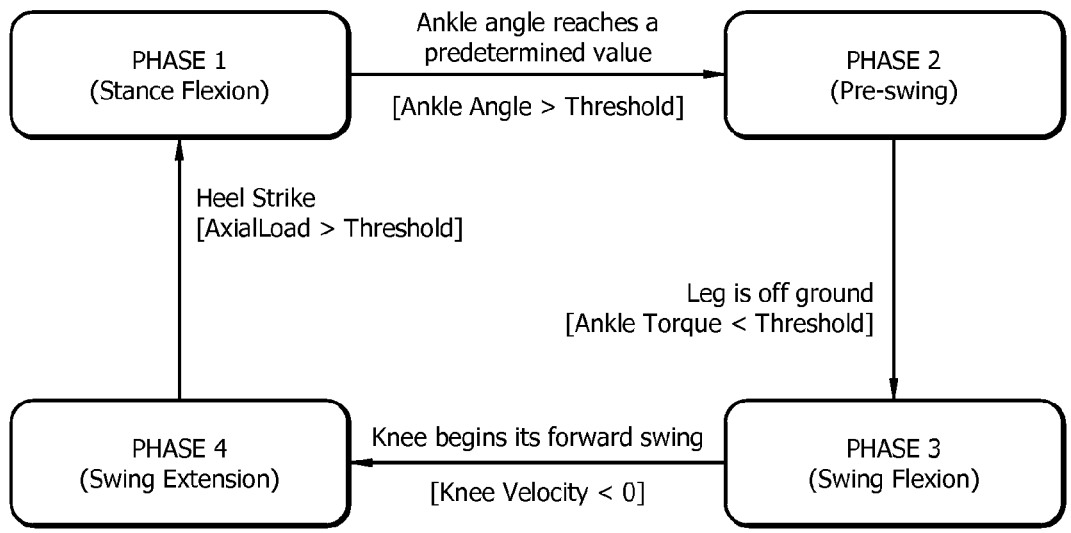
FIG. 9 shows a finite-state model of normal walking, according to an embodiment of the invention. Each box represents a different internal phase and the transition conditions between the internal phases are specified.

FIG. 9 shows exemplary switching rules between internal phases for walking. FIG. 16 shows another set exemplary switching rules, for walking, standing, and sitting activity modes. As described above, if the user does not initiate actions that trigger the next phase (e.g. based on the switching rules), the prosthesis will cease to receive power and will come to rest at the local equilibrium identified with the present phase. For example, switching can be based on the ankle angle>a threshold value (mode 1 to mode 2), or ankle torque<threshold) (mode 2 to mode 3), the angle or torque measurements provided by on board sensors as described above.

Phase 1 shown in FIG. 8 begins with a heel strike by the user (which can be sensed by the heel force sensor), upon which the knee immediately begins to flex so as to provide impact absorption and begin loading, while the ankle simultaneously plantarflexes to reach a flat foot state. Both knee and ankle joints have relatively high stiffness (and can be accounted for by k1 in equation 1) during this phase to prevent buckling and allow for appropriate stance knee flexion, because phase 1 comprises most of the weight bearing functionality. Phase 2 is the push-off phase and begins as the ankle dorsiflexes beyond a given angle (i.e. user's center of mass lies forward of stance foot). The knee stiffness decreases in this mode to allow knee flexion while the ankle provides a plantarflexive torque for push-off. Phase 3 begins as the foot leaves the ground as detected by the ankle torque load cell and lasts until the knee reaches maximum flexion. Mode 4 is active during the extension of the knee joint (i.e. as the lower leg swings forward), which begins as the knee velocity becomes negative and ends at heel strike (e.g. as determined by the heel force sensor).

In both of the swing phases (Phases 3 and 4), the ankle torque can be small and can be represented in the controller as a (relatively) weak spring regulated to a neutral position. The knee can be primarily treated as a damper in both swing phases.

Figure 10:
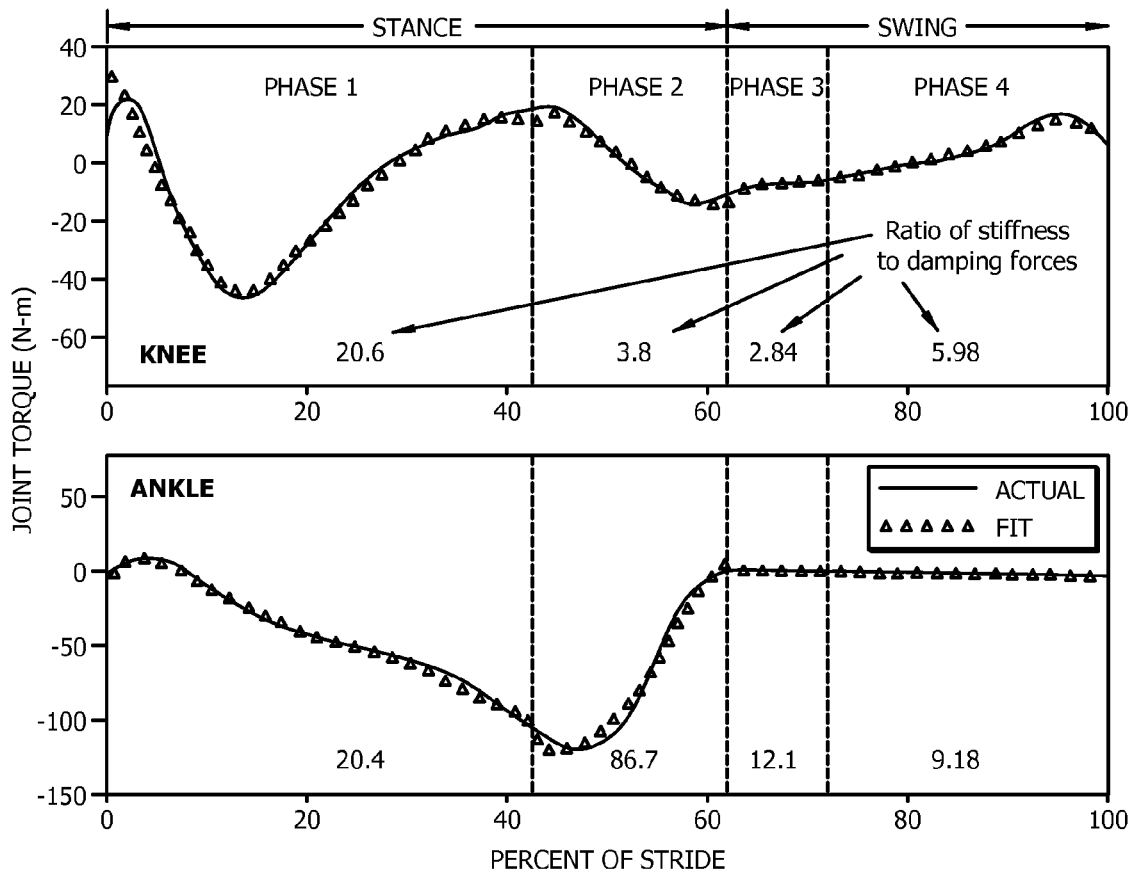
FIG. 10 shows piecewise fitting of knee and ankle torques during normal speed level walk scaled for a 75 kg adult to a non-linear spring-damper impedance model.

Impedance modeling of joint torques was preliminarily validated by utilizing the gait data from a healthy 75 kg subject, as derived from body-mass normalized data. Incorporating the four internal phases described above, along with the motion and torque data for each joint, a constrained least-squares optimization was conducted to generate a set of parameters $k_1$, b and $\theta_e$ for each phase for each joint for use in Equation 1. The resulting parameter set can be fit to joint torques and is shown graphically in FIG. 10. FIG. 10 shows piecewise fitting of knee and ankle torques during normal speed level walk scaled for a 75 kg adult to a non-linear spring-damper impedance model. The numbers shown in each phase represent the mean ratio of the stiffness forces to damping forces predicted by the fit. The vertical lines represent the segmentation of a gait stride into four distinct phases. The fit shown in FIG. 10 clearly indicates that normal joint function can be represented by the use of piecewise passive functions.

Controllers according to embodiments of the invention generally comprise an underlying gait controller (intra-modal controller). An optional supervisory gait controller (also called intent recognizer) can also be provided. Both controllers generally utilize measured information. This information generally comprises user and ground interaction forces (F) and moments/torques (τ), joint angles and angular velocities from on-board sensors, and can be used to extract real-time input from the user. The gait control component utilizes the sensed instantaneous nature of the user input (i.e., moments and forces) to control the behavior of the leg within a given activity mode, such as standing, walking, or stair climbing.

Figure 11:
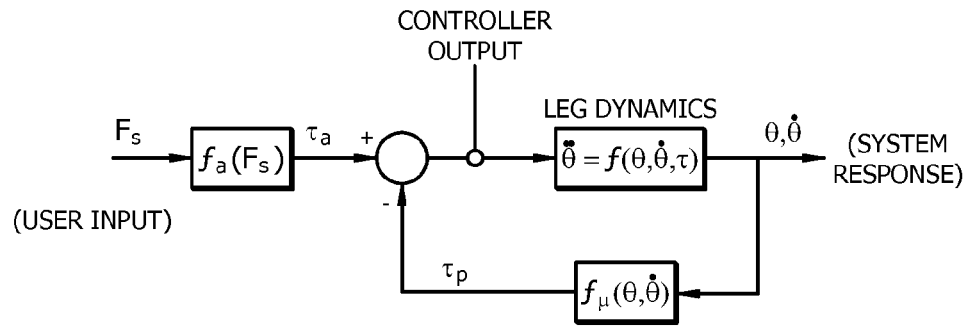
FIG. 11 is a diagram for an active/passive decomposition based control of the powered knee and ankle prosthesis, according to an embodiment of the invention.
Figure 12:
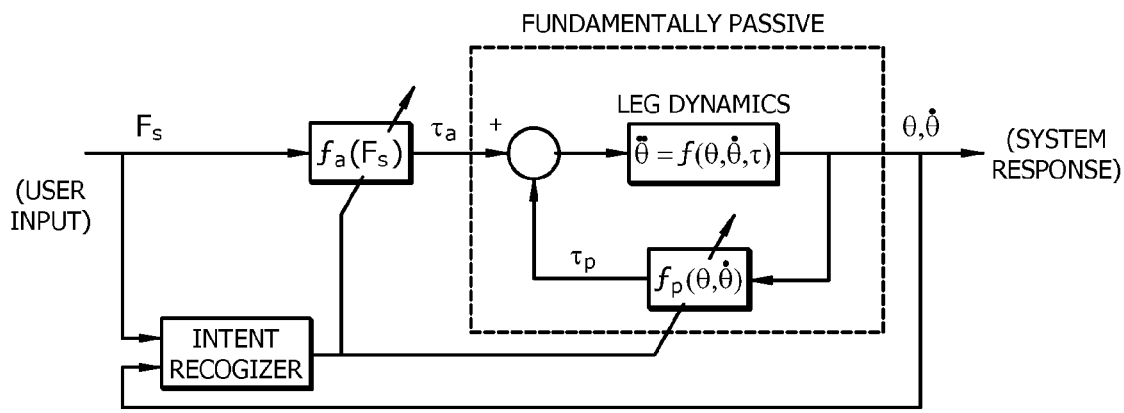
FIG. 12 is a diagram for a general form of active-passive decomposition control including intent recognition that provides supervisory modulation, according to an embodiment of the invention.

Two exemplary approaches to intra-modal impedance generation are described below. The first approach is shown in FIG. 11 and represents a general form of active-passive decomposition-based intra-mode control. The second embodiment shown in FIG. 12 includes the control structure shown in FIG. 11 but adds a supervisory intent recognizing controller to modulate the intra-modal control based on inputs from an intent recognition module. As shown in FIGS. 11 and 12, $F_s$ is the force the user of the prosthesis is applying, such as a heel force in the case of a heel strike, τ represents joint torque, and θ represent joint angles. $\tau_a$ represents the active component of joint torque which is roughly proportional to the input force, and $\tau_p$ represents the passive component of torque. The active joint torque $\tau_a$ is thus the total joint torque τ minus the passive joint torque, τp. Derivatives are shown using the dot convention, with one dot being the first derivative (e.g., $\dot{\theta}$ being angular velocity) and two dots representing the second derivative.

Intra-Modal Active-Passive Decomposition Control

In this embodiment of the intra-modal controller, shown in FIG. 11, the behavior of the prosthesis can be decomposed into a passive component and an active control component. The active control component is an algebraic function of the user's real-time input $F_s$ (i.e., sensed socket-prosthesis interface forces and moments and sensed ground reaction forces). The controller output is shown as the active torque ($\tau_a$) minus the passive torque $\tau_p$. The controller output $\tau_a$-$\tau_p$ applied to the prosthetic leg based on dynamics of the leg responds via θ and $\dot{\theta}$. The system response, θ and $\dot{\theta}$, is fed back to the controller.

Power applied to the prosthesis can be thus commanded directly by the user through measured interface forces and moments initiated by user movements. In the absence of these commands from the user, $F_s$=0, $\tau_a$=0 and the prosthesis fundamentally (by virtue of the control structure) cannot generate power, and thus only exhibits controlled passive behavior. Due to the decomposition of energetic behaviors inherent in this control structure, the prosthesis under it's own control can be generally stable and passive. Unlike known echo control approaches, the input can be real-time, based only on the affected leg, and thus the approach can be equally applicable to bilateral and unilateral amputees and can reflect the instantaneous intent of the user. Additionally, unlike echo control that is based on servocontrol, the prosthesis will exhibit a natural impedance to the user that should feel more like a natural limb. These combined features should result in an active prosthesis that will feel inasmuch as possible like a natural extension of the user. The structure and properties of both the gait controller and intent recognizer are described below.

As described above, since gait is largely a periodic activity, joint behavior can be functionally decomposed over a period by decomposing the joint torque into a passive component and an active component. The passive component can comprise a function of angle (i.e., single-valued and odd), and a function of angular velocity passive (i.e., single-valued and odd), such as equation 1 described above. The active component can be a function of the user input (i.e., socket interface forces). Given a set of data that characterizes a nominal period of joint behavior, the passive component can be first extracted from the whole, since the passive behavior is a subset of the whole (i.e., the passive component consists of single-valued and odd functions, while the active has no restrictions in form). The passive component can be extracted by utilizing a least squares minimization to fit a generalized singled-valued odd function of angle and angular velocity to the torque. Once the passive component is extracted, the residual torque (i.e., the portion that is not extracted as a passive component), can be constructed as an algebraic function of the sensed socket interface and ground reaction forces (i.e., the direct-acting user input) by incorporating a similar candidate function, but not restricted to be of passive form. Finally, superimposing the passive and active components provides a decomposed functional approximation of the original period joint torque.

Intra-Modal Locally Passive Event-Triggered Control

In this embodiment of the intra-modal controller shown in FIG. 12, a supervisory intent recognizer can be added that utilizes the same sensed user inputs (i.e., moments and forces) as the intra-modal/gait controller, but extracts the user's intent based on the characteristic shape of the user input(s) and system response (e.g. F, θ, θ-dot). Based on the extracted intent, the supervisory intent recognizer modulates the behavior of the underlying gait controller to smoothly transition behavior within a gait (e.g., speed and slope accommodation) and between gaits (e.g., level walk to stair ascent), thus offering a unified control structure within and across all gaits.

Gait intent recognition can be a real time pattern recognition or signal classification problem. The signal in this case is generally the combination of socket interface forces Fs and the dynamic state of the prosthesis, which in one embodiment can be a vector of the knee and ankle angles θ for a powered leg prosthesis according to an embodiment of the invention. A variety of methods exist for pattern recognition and signal classification including nearest neighbor algorithms, neural networks, fuzzy classifiers, linear discriminant analysis, and genetic algorithms.

Sensors

Figure 13A:
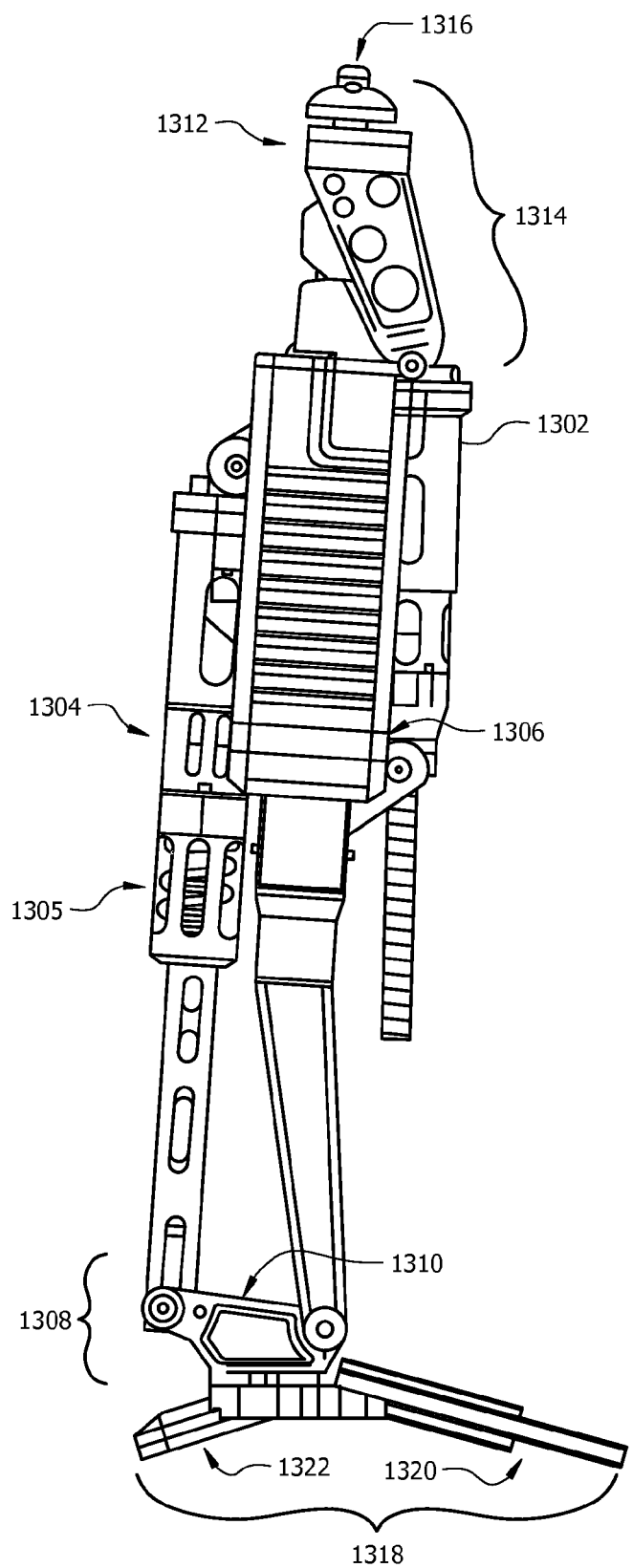
FIG. 13A is a side view of powered knee and ankle prosthesis, according to another embodiment of the invention.
Figure 13B:
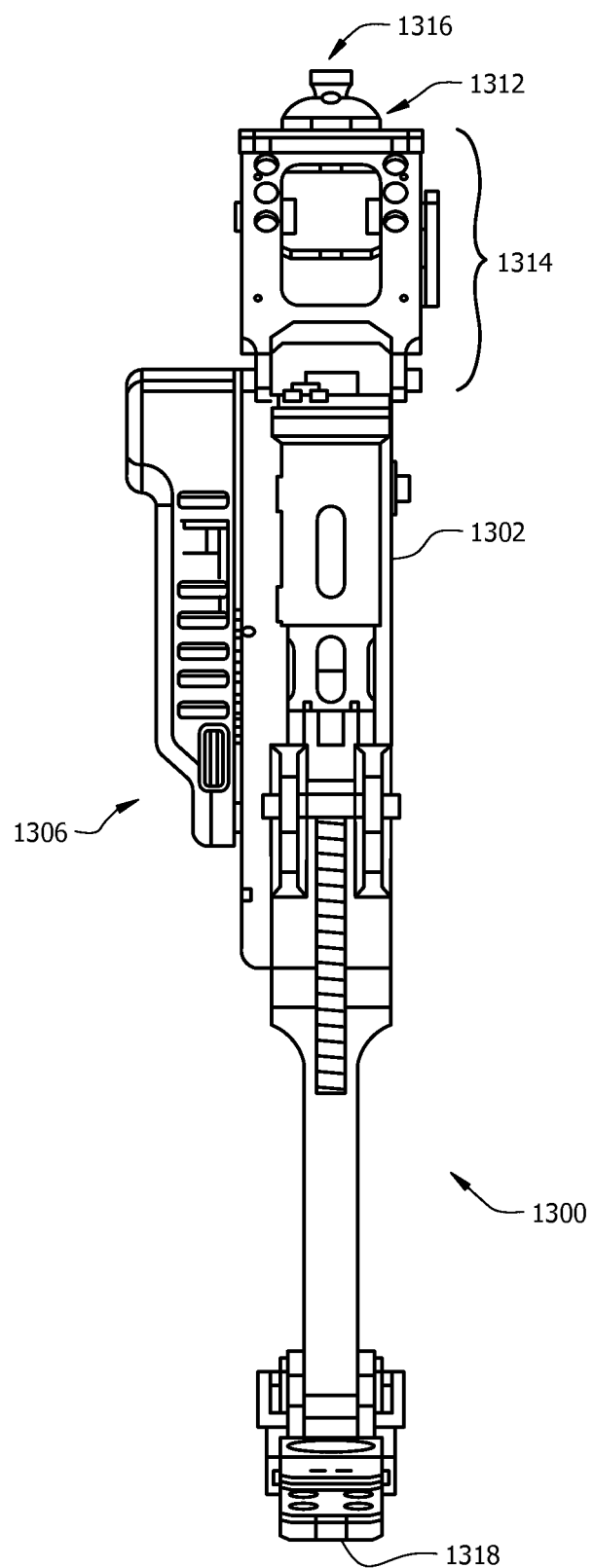
FIG. 13B is a front view of powered knee and ankle prosthesis of FIG. 13A.
Figure 14A:
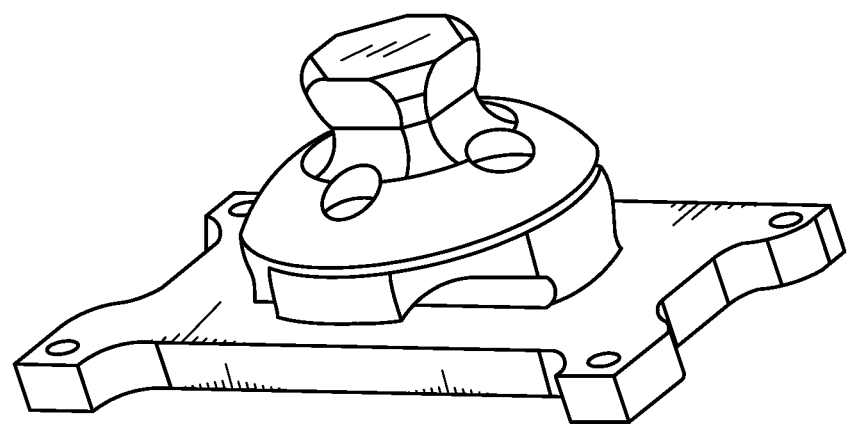
FIGS. 14A and 14B show perspective and bottom views of an exemplary sagittal moment load cell suitable for use in the various embodiments of the invention.
Figure 14B:
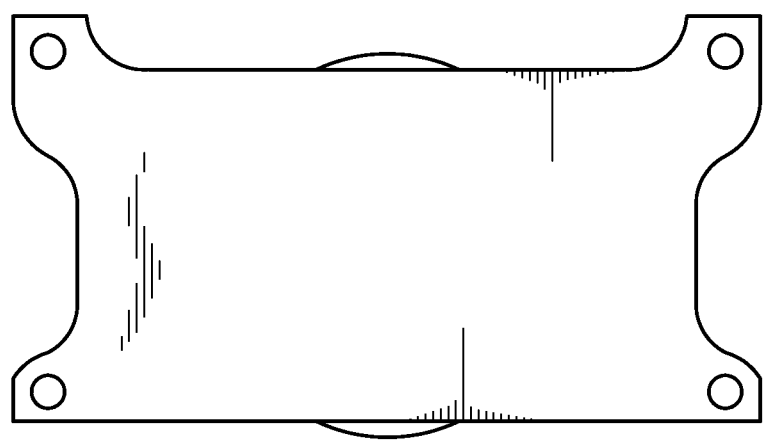

As described above embodiments of the invention include a number of sensors for providing signals for adjusting operation of a leg and ankle prosthesis. A description of one exemplary arrangement of sensors can be described below with respect to FIGS. 13A, 13B, 14A, and 14B. FIG. 13A is a side view of powered knee and ankle prosthesis 1300, according to another embodiment of the invention. FIG. 13B is a front view of powered knee and ankle prosthesis of FIG. 13A. FIGS. 14A and 14B show perspective and bottom views of an exemplary sagittal moment load cell suitable for use in the various embodiments of the invention.

Each joint actuation unit, such as knee actuation unit 1302 and ankle actuation unit 1304 in FIG. 13k can include a uniaxial load cell positioned in series with the actuation unit for closed loop force control. Both the knee and ankle joints can incorporate integrated potentiometers for joint angle position. The ankle actuation unit can include a spring 1305, as described above with respect to FIGS. 1A-4. One 3-axis accelerometer can be located on the embedded system 1306 and a second one can located below the ankle joint 130X on the ankle pivot member 1310. A strain based sagittal plane moment sensor 1312, such as sensor 1400 shown in FIGS. 14A and 14B, can located between the knee joint 1314 and the 1316 the socket interface 1316, which measures the moment between a socket and the prosthesis. In the various embodiments of the invention, a sagittal plane moment sensor can be designed to have a low profile in order to accommodate longer residual limbs. The sensor can incorporate a full bridge of semiconductor strain gages which measure the strains generated by the sagittal plane moment. In one embodiment of the invention, the sagittal plane moment sensor was calibrated for a measurement range of 100 Nm. A custom foot 1318 can designed to measure the ground reaction force components at the ball 1320 of the foot and heel 1322. The foot can include of heel and ball of foot beams, rigidly attached to a central fixture and arranged as cantilever beams with an arch that allows for the load to be localized at the heel and ball of the foot, respectively. Each heel and ball of foot beam can also incorporates a full bridge of semiconductor strain gages that measure the strains resulting from the respective ground contact forces. In one embodiment of the invention, the heel and ball of foot load sensors were calibrated for a measurement range of 1000 N. In addition, incorporating the ground reaction load cell into the structure of a custom foot can eliminate the added weight of a separate load cell, and also enables separate measurement of the heel and ball of foot load. The prosthetic foot can be designed to be housed in a soft prosthetic foot shell (not shown).

Microcontroller System

The powered prosthesis contains an embedded microcontroller that allows for either tethered or untethered operation. An exemplary embedded microcontroller system 1500 is shown in the block diagram in FIG. 15. The embedded system 1500 consists of signal processing, power supply, power electronics, communications and computation modules. The system can be powered by a lithium polymer battery with 29.6 V. The signal electronics require +/−12 V and +3.3 V, which are provided via linear regulators to maintain low noise levels. For efficiency, the battery voltage can be reduced by PWM switching amplifiers to +/−15 V and +5 V prior to using the linear regulators. The power can be disconnected via a microcontroller that controls a solid state relay. The power status can be indicated by LED status indicators controlled also by the microcontroller.

The analog sensor signals acquired by the embedded system include the prosthesis sensors signals (five strain gage signals and two potentiometer signals), analog reference signals from the laptop computer used for tethered operation, and signals measured on the board including battery current and voltage, knee and ankle servo amplifier currents and two 3-axis accelerometers. The prosthesis sensor signals are conditioned using input instrumentation amplifiers. The battery, knee motor and ankle motor currents are measured by current sense resistors and current sensing amplifiers. The signals are filtered with a first-order RC filter and buffered with high slew rate operational amplifiers before the analog to digital conversion stage. Analog to digital conversion can be accomplished by two 8-channel analog to digital converters. The analog to digital conversion data can be transferred to the microcontroller via serial peripheral interface (SPI) bus.

Figure 15:
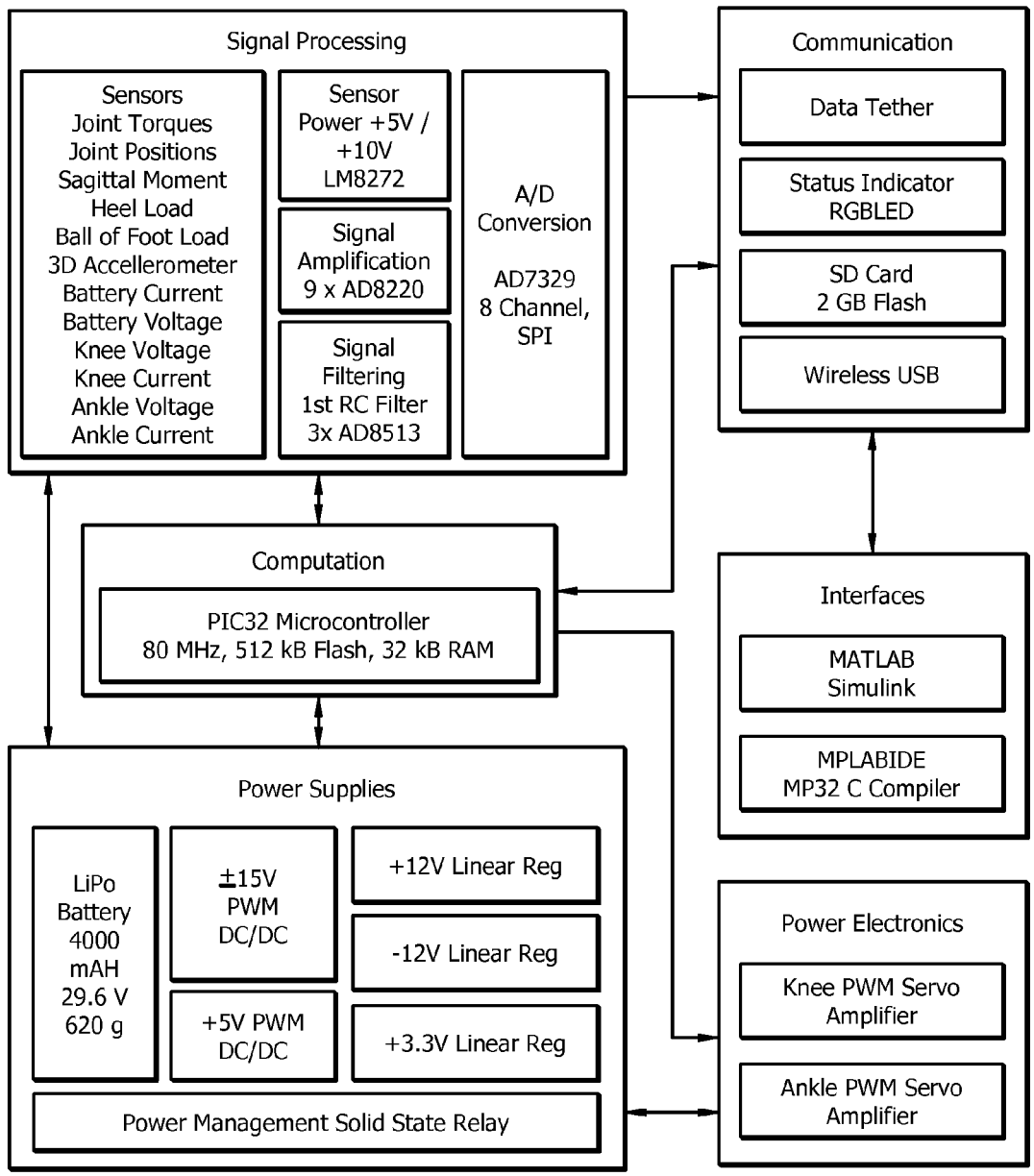
FIG. 15 is a block diagram of an exemplary embedded microcontroller in accordance with an embodiment of the invention.

The computation module of the embedded system can be a 32-bit microcontroller, or processor, for generating control signals for other modules, and its associated memory (e.g., Flash memory and Random Access Memory or RAM depicted in FIG. 15). In the untethered operation state, the micro controller performs the servo and activity controllers of the prosthesis and data logging at each sample time. In addition to untethered operation, the prosthesis can also be controlled via a tether by a laptop computer running MAT LAB Simulink RealTime Workshop. In the tethered operation state, the microcontroller drives the servo amplifiers based on analog reference signals from the laptop computer. A memory card can be used for logging time-stamped data acquired from the sensors and recording internal controller information. The memory chip can be interfaced to the computer via wireless USB protocol. The microcontroller sends PWM reference signals to two four quadrant brushless DC motor drivers with regenerative capabilities in the second and forth quadrants of the velocity/torque curve.

Control of Sitting and Standing

Figure 17:
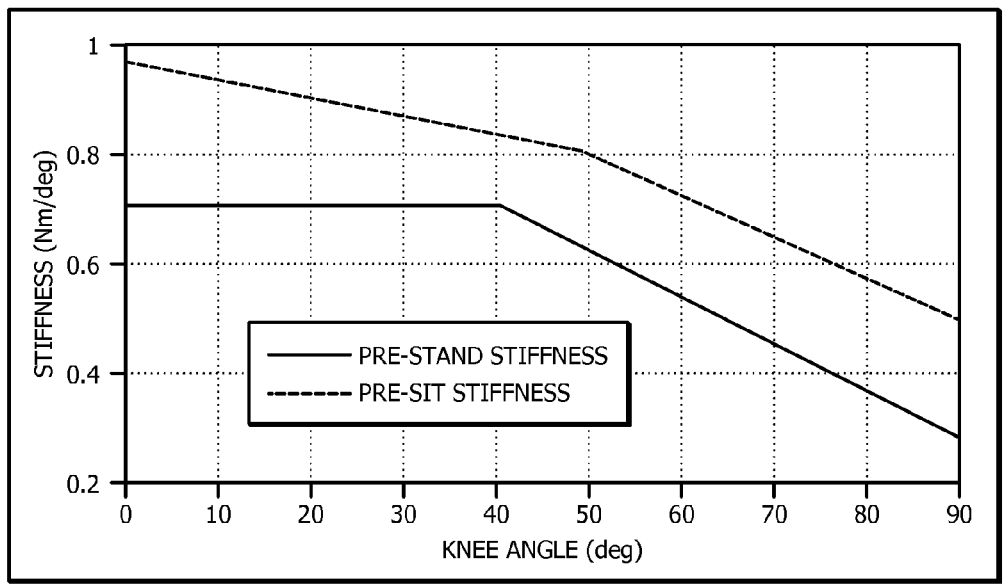
FIG. 17 shows knee angle modulated knee stiffness during pre-stand (solid line) and pre-sit (dashed line) phases.

In some embodiments of the invention, additional controls can be provided for operating the prosthesis when going from a sitting to a standing position or vice versa. This can be implemented via the use of a sitting mode controller implemented in the microcontroller. Operation of the sitting mode controller consists of four phases that are outlined in the general control state chart shown in FIG. 16. As shown in FIG. 16, two phases are primary sitting phases, weight bearing and non-weight bearing. The other two phases encompass the transition phases, pre-stand and pre-sit, for standing up and sitting down, respectively. Weight bearing and non-weight bearing are the primary sitting phases that switch the knee and ankle joints between high and low impedances, respectively. The transition phases, pre-stand and pre-sit, modulate the stiffness of the knee as a function of knee angle, as shown in FIG. 17, to assist the user in standing up and sitting down. FIG. 17 shows knee angle modulated knee stiffness during pre-stand (solid line) and pre-sit (dashed line) phases.

The modulation allows for smoother transitions near the seated position. The ankle joint can be slightly dorsiflexed with moderate stiffness during the standing up and sitting down phases. Switching between the four sitting phases occurs when sensor thresholds are exceeded, as depicted FIG. 16. The parameters of the impedance based controllers are tuned using a combination of feedback from the user and joint angle, torque and power data from the prosthesis.

Mechanical Design

In the various embodiments of the invention, actuation for the prosthesis can be provided by two motor-driven ball screw assemblies that drive the knee and ankle joints, respectively, through a slider-crank linkage. The prosthesis can be capable of 120° of flexion at the knee and 45° of planterflexion and 20° of dorsiflexion at the ankle. In one embodiment, each actuation unit consists of a DC motor (such as a Maxon EC30 Powermax) connected to a 12 mm diameter ball screw with 2 mm pitch, via helical shaft couplings. An exemplary ankle actuation unit additionally incorporates a 302 stainless steel spring (51 mm free length and 35 mm outer diameter), with 3 active coils and a stiffness of 385 N/cm in parallel with the ball screw.

Figure 18:
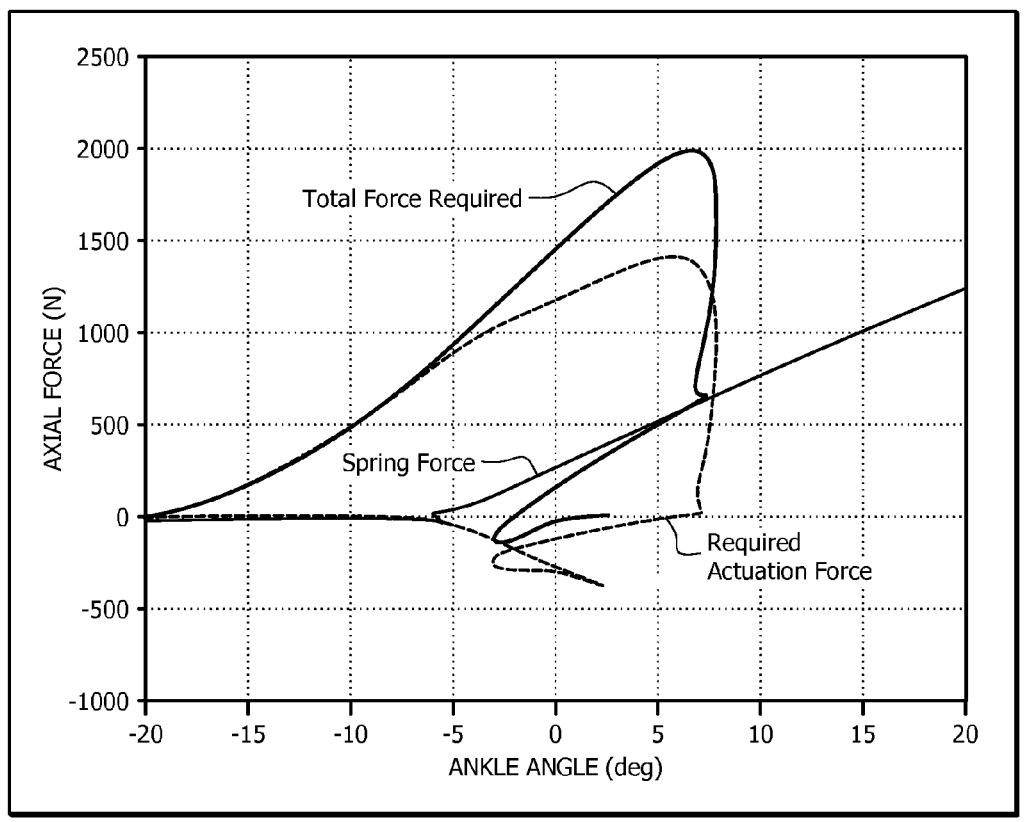
FIG. 18 is a plot of axial actuation unit force versus ankle angle.

As described above with respect to FIGS. 1A-4, the purpose of the spring can be to bias the motor's axial force output toward ankle plantarflexion, and to supplement power output during ankle push off. The stiffness of the spring can be maximized to allow for peak force output without limiting the range of motion at the ankle. The resulting axial actuation unit's force versus ankle angle plot can be shown in FIG. 18. FIG. 18 is a plot if axial force as a function of ankle angle illustrating spring force, actuator force and total force. FIG. 18 graphically demonstrates for fast walking the reduction in linear force output supplied by the motor at the ankle through the addition of the spring. Note that the compression spring does not engage until approximately five degrees of ankle plantarflexion. Each actuation unit can include a uniaxial load cell (such as Measurement Specialties ELPF-500L), positioned in series with the actuation unit for closed loop force control of the motor/ballscrew unit. Both the knee and ankle joints can incorporate bronze bearings and, for joint angle measurement, integrated precision potentiometers (such as an ALPS RDC503013). A strain based sagittal plane moment sensor, as previously described with respect to FIGS. 14A and 14B can be located between the knee joint and the socket interface, which measures the moment between the socket and prosthesis. The ankle joint connects to a foot, which incorporates strain gages to measure the ground reaction forces on the ball of the foot and on the heel. The central hollow structure houses a lithium-polymer battery and provides an attachment point for the embedded system hardware. To better fit with an anthropomorphic envelope, the ankle joint can be placed slightly anterior to the centerline of the central structure. This gives the prosthesis the illusion of flexion when the amputee can be standing vertically with the knee fully extended.

The length of the shank segment can be varied by changing the length of three components; the lower shank extension, the spring pull-down, and the coupler between the ball nut and ankle. Additional adjustability can be provided by the pyramid connector that can be integrated into the sagittal moment load cell for coupling the prosthesis to the socket (as is standard in commercial transfemoral prostheses). In one embodiment of the invention, the self-contained transfemoral prosthesis was fabricated from 7075 aluminum and has a total mass of 4.2 kg, which can be within an acceptable range for transfemoral prostheses, and comparable to a normal limb segment. A weight breakdown of an exemplary device is presented below in Table I.

TABLE II

MASS BREAKDOWN OF SELF-CONTAINED POWERED PROSTHESIS.

| Component | Mass (kg) |
| --- | --- |
| Battery | 0.62 |
| Electronics | 0.36 |

TABLE II-continued

MASS BREAKDOWN OF SELF-CONTAINED POWERED PROSTHESIS.

| Component | Mass (kg) |
| --- | --- |
| Knee Motor Assembly | 0.72 |
| Ankle Motor Assembly | 0.89 |
| Sensorized Foot | 0.35 |
| Foot Shell | 0.24 |
| Sagittal Moment Sensor | 0.12 |
| Remaining Structure | 0.90 |
| Total Weight | 4.20 |

Passive joint torque, $\tau_p$, can be defined as the part of the joint torque, $\tau$, which can be represented using spring and dashpot constitutional relationships (passive impedance behavior). The system can only store or dissipate energy due to this component. The active part can be interpreted as the part which supplies energy to the system and the active joint torque can be defined as $\tau_a = \tau - \tau_p$. This active part can be represented as an algebraic function of the user input via the mechanical sensory interface (i.e socket interface forces and torques).

Figure 19:
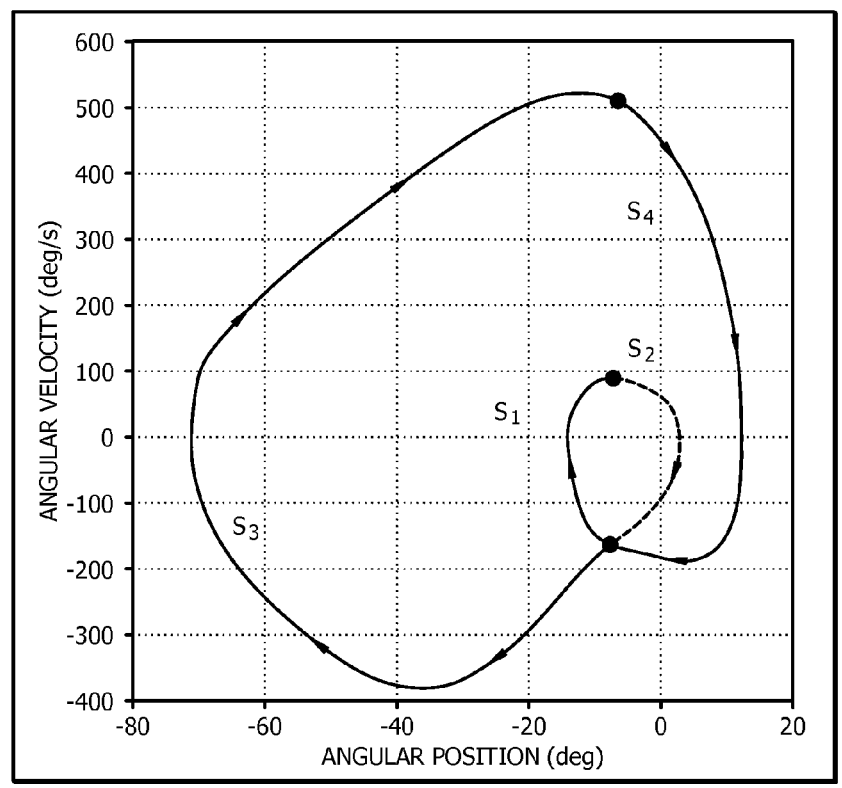
FIG. 19 shows a normal speed walking phase portrait of the knee joint and four stride segments.

Gait is considered a mainly periodic phenomena with the periods corresponding to the strides. Hence, the decomposition of a stride will give the required active and passive torque mappings for a specific activity mode. In general, the joint behavior exhibits varying active and passive behavior in each stride. Therefore, segmenting of the stride in several parts can be necessary. In this case, decomposition of the torque over the entire stride period requires the decomposition of the different segments and piecewise reconstruction of the entire segment period. In order to maintain passive behavior, however, the segments cannot be divided arbitrarily, but rather can only be segmented when the stored energy in the passive elastic element is zero. This requires that the phase space can only be segmented when the joint angle begins and ends at the same value. FIG. 19 shows the phase portrait of normal speed walking and the four different stride segments, $S_1$, $S_2$, $S_3$ and $S_4$. Thus, the entire decomposition process consists of first appropriate segmentation of the joint behavior, followed by the decomposition of each segment into its fundamental passive and active components.

Figure 20:
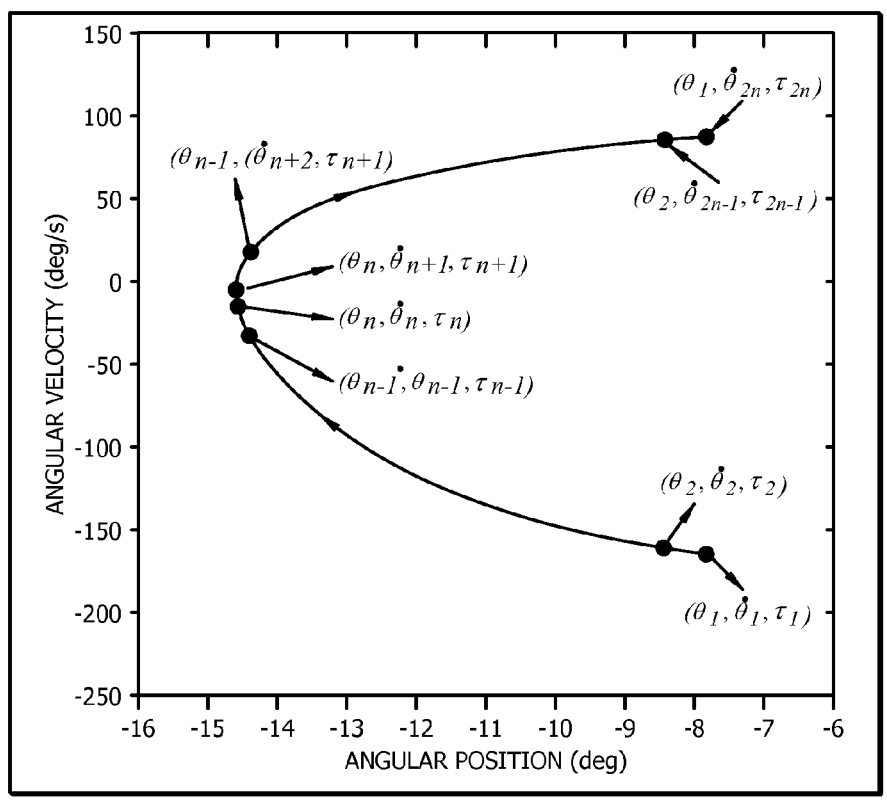
FIG. 20 shows the selection of indexing data samples during a first segment of a walking stride.

The decomposition of each segment shown in FIG. 19 can be converted to an optimization problem. In each segment of the stride, 2n data points are selected by sampling the angular position in equal intervals between its minimum and maximum and selecting the corresponding positive and negative angular velocities. In this work, the number of angular position samples for each segment, n can be set to be 100. The constrained least squares optimization problem given in Equation 2 below can be constructed and solved.

$$\min_x \frac{1}{2}\|Cx - d\|_2^2 \quad (2)$$
$$\text{s.t.} \quad 0 \le x$$

where C, x and d are defined in Equations 3, 4, and 5 below, respectively. The indexing of the joint angular position, angular velocity and moment samples are explained via the sketch in FIG. 20. FIG. 20 shows a selection and indexing of data samples from a first segment.

$$C_{4n \times 3n} = [C_1 \ C_2 \ C_3]^T \quad (3)$$

$$C_1 = \begin{bmatrix} \mathrm{diag}\left(\begin{bmatrix}\theta_1\\\theta_2\\\vdots\\\theta_n\end{bmatrix}_{n\times 1} - \alpha\right) & \mathrm{diag}\left(\begin{bmatrix}\dot\theta_1\\\dot\theta_2\\\vdots\\\dot\theta_n\end{bmatrix}_{n\times 1}\right) \\ \mathrm{diag}\left(\begin{bmatrix}\theta_n\\\theta_{n-1}\\\vdots\\\theta_1\end{bmatrix}_{n\times 1} - \alpha\right) & \mathrm{diag}\left(\begin{bmatrix}\vdots\\\dot\theta_n\end{bmatrix}_{2n\times 1}\right) \end{bmatrix}_{2n \times 3n}$$

$$C_2 = \begin{bmatrix} C_{21} & C_{23} \\ C_{22} & \end{bmatrix}_{2n-1 \times 3n}$$

$$C_{21} = \begin{bmatrix} \theta_1 & -\theta_2 & 0 & \cdots & 0 \\ 0 & \ddots & \ddots & \ddots & \vdots \\ \vdots & \ddots & \theta_{n-1} & \theta_n & 0 \\ 0 & \cdots & 0 & 0 & 0 \end{bmatrix}_{n \times n}$$

$$C_{22} = \begin{bmatrix} \theta_n & -\theta_{n-1} & 0 & \cdots & 0 \\ 0 & \ddots & \ddots & \ddots & \vdots \\ \vdots & \ddots & \theta_3 & -\theta_2 & 0 \\ 0 & \cdots & 0 & \theta_2 & -\theta_1 \end{bmatrix}_{n-1 \times n}$$

$$C_{23} = \begin{bmatrix} \dot\theta_1 & -\dot\theta_2 & 0 & \cdots & 0 \\ 0 & \ddots & \ddots & \ddots & \vdots \\ \vdots & \ddots & \dot\theta_{2n-2} & -\dot\theta_{2n-1} & 0 \\ 0 & \cdots & 0 & \dot\theta_{2n-2} & -\dot\theta_{2n} \end{bmatrix}_{2n-1 \times 2n}$$

$$C_3 = [\beta \ \beta \ \cdots \cdots \ \beta \ \beta]_{1 \times 3n}$$

$$x_{3n \times 1} = \begin{bmatrix} k_1 \\ k_2 \\ \vdots \\ k_{n-1} \\ k_n \\ b_1 \\ b_2 \\ \vdots \\ b_{2n-1} \\ b_{2n} \end{bmatrix} \quad (4)$$

$$d_{4n \times 1} = \begin{bmatrix} \tau_1 \\ \tau_2 \\ \vdots \\ \tau_{2n-1} \\ \tau_{2n} \\ \tau_1 - \tau_2 \\ \tau_2 - \tau_3 \\ \vdots \\ \tau_{2n-1} - \tau_{2n} \\ 0 \end{bmatrix} \quad (5)$$

The matrix C consists of three sub-matrices, $C_1$, $C_2$ and $C_3$. $C_1$ can be the main part responsible for the fitting of the spring and dashpot constants, k and b. $C_2$ bounds the rate of change of the passive joint torque and ensures smoothness in the resulting passive joint torque, and $C_3$ is basically a row of penalty constants, $\beta$, which penalizes large values of the spring and dashpot constants and thus limits the magnitudes of both. In this work, $\beta$ is set to 0.1.

The origin of each virtual spring can be also added to the optimization problem formulation as a parameter in order to obtain a tighter passive torque fit. Therefore, the optimization problem given by (3) can be solved iteratively for a range of values of spring origin constant, $\alpha$. The solution with the least error norm can be selected as the optimal solution.

Figure 21A:
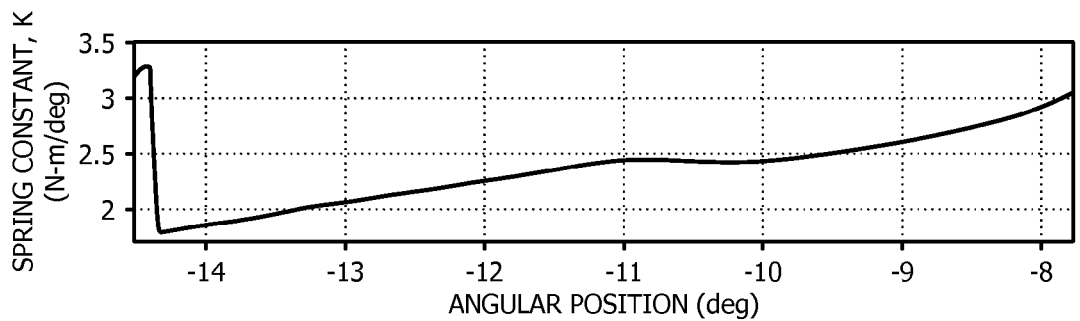
FIGS. 21A, 21B, and 21C are the output of the decomposition for Segment 1 showing the spring and dashpot constants and the active and passive knee torques.
Figure 21B:
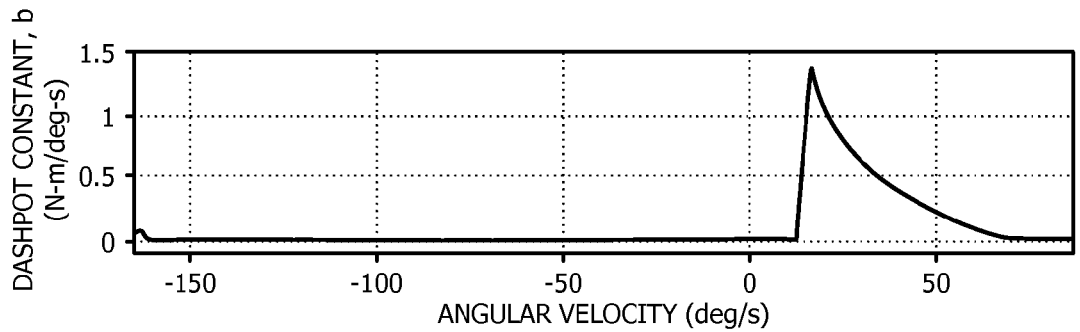
Figure 21C:
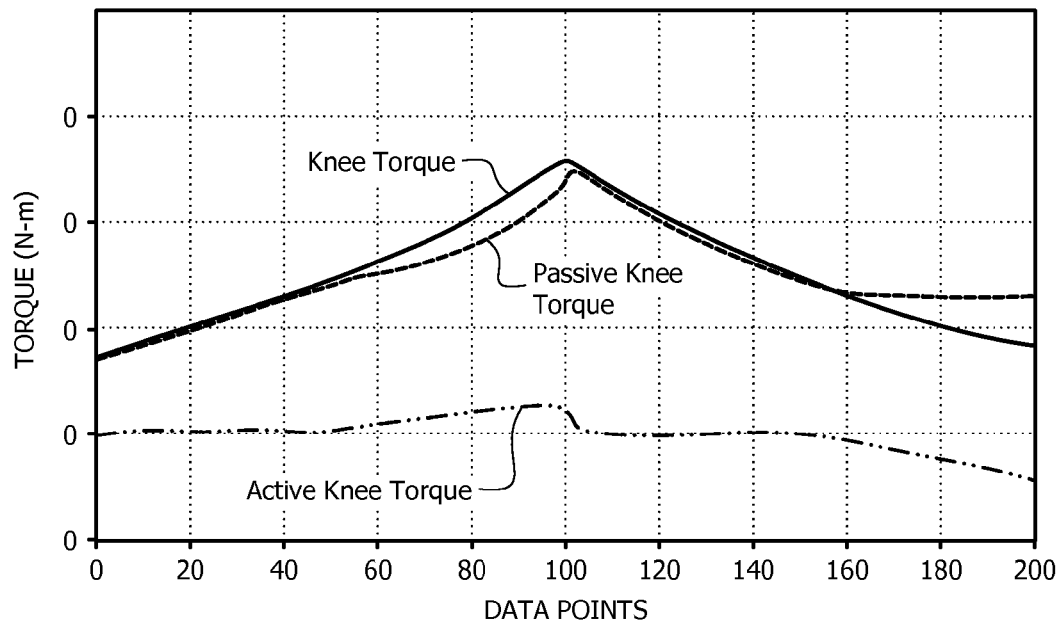

The result of the above stated constrained optimization problem for segment 1 can be shown in FIGS. 21A, 21B, and 21C. FIGS. 21A-21C are the output of the decomposition for $s_1$ in FIG. 19 showing the spring and dashpot constants and the active and passive knee torques (Spring origin, $_\alpha$, is 23 degrees).

As can be seen from FIGS. 21A-21C, the decomposed passive part can be very similar to the joint torque, and thus it can be stated that the behavior of the joint can be mainly passive. The result of the decomposition for the segment $S_i$ can be stored in $R_i$ of the form given in Equation 6.

$$R_i = [\theta \dot{\theta} \tau_{pas} F_{S1} F_{S2} \tau_{act}]_{2n \times 6} \quad (6)$$

where $\pi_{pas} = C_1 x$.

The procedure presented above decomposes the joint torques into active and passive parts. The joint torque references for the control of the prosthesis are generated by combining this active and passive torques. There are two major challenges to be solved. Firstly, the correct motion segment must be selected. Secondly, after the motion segment is selected at each sampling instant a new joint torque reference can be generated using the discrete mappings for the active and passive torque parts.

Figure 22:
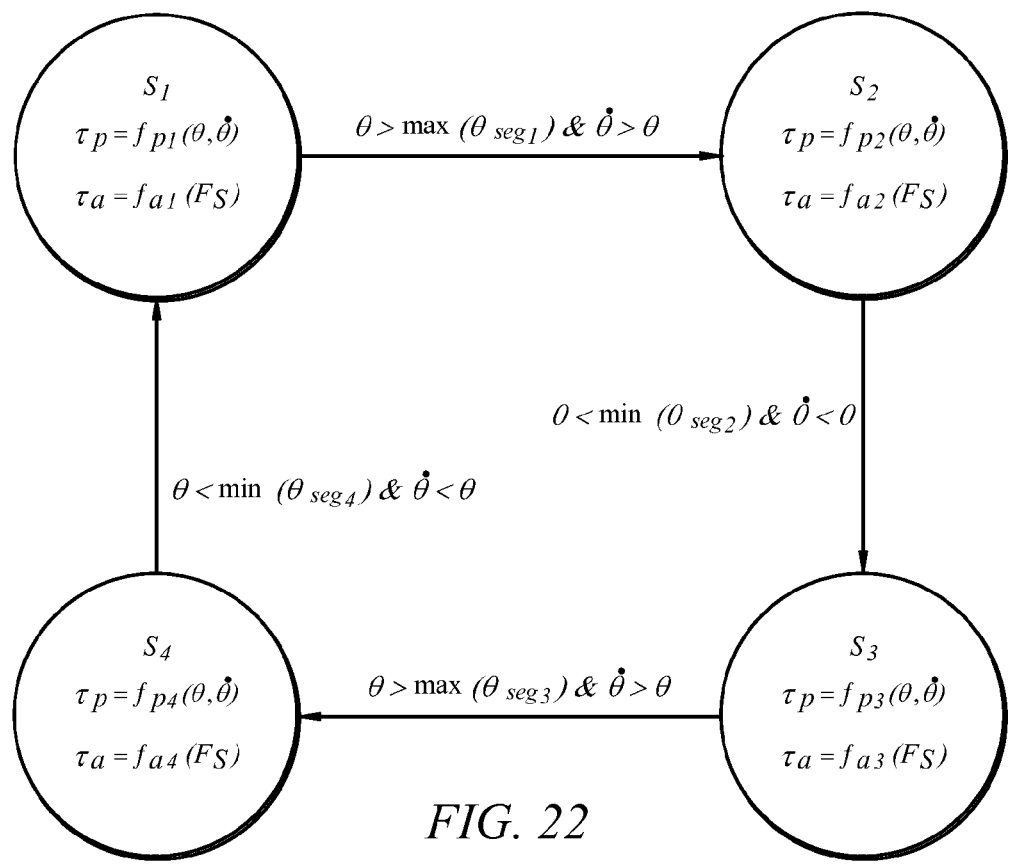
FIG. 22 is a state chart for governing the discrete dynamics of an active-passive decomposition controller in accordance with an embodiment of the invention.

A switching system modeling approach incorporating both discrete and continuous states can be used for the reconstruction of the torque reference signal. The state chart shown in FIG. 22. will govern the discrete dynamics of the controller. Since the sequence of the segments can be ordered (i.e., the direction of the motion for a specific gait phase does not change), each segment can transition only to the next one, where the transition guard function can be written as a inequality in terms of $\theta$ and $\dot{\theta}$. The transitions between segments take no time and the dynamics of the controller are governed by the $\{f_{Pi}(\theta,\dot{\theta}); f_{a_i}(F_S)\}$ pair at each sampling instant. The joint reference torque is $$\tau_{ref} = \tau_a \tau_p = f_{pi}(\theta,\dot{\theta}) + f_{a_i}(F_S) \quad (7)$$

The decomposition algorithm presented above gives the result matrix, R, for each segment. The discrete data in R can be used to construct the joint torque reference for the continuous measurements of another trial in the same gait phase. At each sampling instant of the algorithm, the measurement vector $m = [\theta_m, \dot{\theta}_m, F_{S1\_m}, F_{S2\_m}]^T$ can be acquired. For the reconstruction of the passive knee torque part, the Euclidian error norm between the $[\theta_m \dot{\theta}_m]^T$ and the angular position and velocities of all the samples in that segment $[\theta_i \dot{\theta}_i]^T$ can be calculated as shown in Equation 8 and stored in the vector e.

$$e_i = \sqrt{(\theta_m - \theta_i)^2 + (\dot{\theta}_m - \dot{\theta}_i)^2} \quad (8)$$

Then two elements of this vector with the least error norm are found and the passive knee torque reference can be found as a weighted linear combination of the passive knee torques corresponding to these points. The reconstruction of the active knee torque part is similar where only $\{\theta,\dot{\theta}, \tau_{pas}\}$ is exchanged with $\{F_{S1}, F_{S2}, \tau_{act}\}$.

Intent Recognition

The supervisory controller (intent recognizer) switches among different underlying intramodal controllers depending on the activity mode the user imposes on the prosthesis. The intent recognizer consists of three parts: activity mode recognizer, cadence estimator and the slope estimator.

The activity mode recognizer detects the activity mode of the prosthesis (standing, walking, sitting, stair ascent or stair descent, etc. . . . ). This can be accomplished by comparing the features which are generated in real time to a feature database using some machine learning and/or pattern recognition methods. The present implementation of the gait mode recognizer, which recognizes standing and walking modes, is described below.

Firstly, a database which contains all the possible activity modes (standing and walking in this case) can be generated by making experimental trials. In the experimental trials, the user can be asked to walk or stand in different controller modes for 50 second long trials. The socket sagittal moment above the knee joint, foot heel load, foot ball load, knee angle, knee velocity, ankle angle and ankle velocity are recorded with 1 ms sampling period. It should be noted that other sensor signals such as accelerations and electromyography measurements from the residual limb can be added to the list of the signals used for intent recognition. For example, from the recorded experimental trials, 10000 random frames (5000 standing and 5000 walking) of 100 samples length are generated for all the seven recorded signals. The mean and the standard deviation of each frame are computed. The mean and standard deviation of signals are selected as the features since minimal computation can be required to obtain them. A database containing 10000 samples with 14 features (mean and standard deviation of the seven signals) belonging to two classes (standing and walking) can be generated. After the database is generated, the dimension of the database can be reduced from 14 to three using principal component analysis (PCA). Dimension reduction can be necessary because pattern recognition for high dimensional datasets can be computationally intensive for real-time applications. After dimension reduction step, the standing and walking data can be modeled with Gaussian mixture models. Gaussian mixture models represent a probability distribution as a sum of several normal Gaussian distributions. The order of the Gaussian mixture model for each mode can be determined according to the Minimum Description Length Criteria.

As described above, the database generation, dimension reduction and the Gaussian mixture modeling are explained. For real-time decision making, overlapping frames of 100 samples can be generated at each 10 ms interval. 14 features described above are extracted from these frames and the PCA dimension reduction can be applied to these features to get a reduced three dimensional feature vector. The reduced dimension features can be fed to the Gaussian mixture models for standing and walking and the probability of the sample vector being standing or walking can be computed. The mode with the greater probability is selected as the instantaneous activity mode. Since one decision might give wrong results in some cases due to noise, disturbance, etc. . . . , a voting scheme can be used to enhance the results. In the voting scheme, the controller activity mode is switched if and only if more than 90 percent of the instantaneous activity mode decisions among the last 40 decisions are a specific activity mode. Once a new activity mode is selected by the voting scheme, the underlying activity controller can be switched to the corresponding mode.

Such an activity mode recognizer is provided by way of illustration and not as a limitation. In the various embodiments of the invention, one or more parts of the algorithm might be modified. For example, in some embodiments, different features such as mean, max, kurtosis, median, AR coefficients, wavelet based features, frequency spectrum based features of the frame might be generated. Additionally, different dimension reduction techniques such as linear discriminant analysis, independent component analysis might be employed. Furthermore, different classification methods such as artificial neural networks, support vector machines, decision trees, hidden Markov models might be used.

Cadence and Slope Estimation

Figure 23:
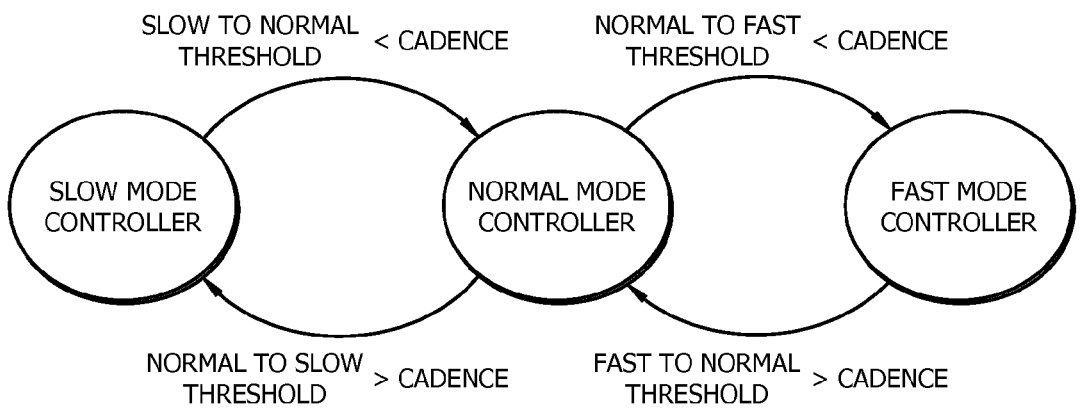
FIG. 23 is a state chart for governing the discrete dynamics of the cadence estimator in accordance with an embodiment of the invention.

Cadence estimation is accomplished by observing peak amplitudes in characteristic signal data and then measuring the time between successive peaks. Since walking is a cyclic activity each of the sensor signals will be periodic of cadence. The most relevant sensor signals will contain only one characteristic amplitude peak per stride such as foot heel load and the ball of foot load. In the real-time implementations, cadence estimation is accomplished by recording the foot load after heel strike when it exceeds 400 N until the load decreases below 350 N. Then, the time of occurrence of the peak load in this window is found and the previous peak time is subtracted from the new peak time. This corresponds to stride time and can be converted to cadence (steps/min) by multiplying with 120. Once the cadence is estimated, the intent recognizer selects the corresponding middle layer controller based on some predefined thresholds as in FIG. 23.

Figure 24:
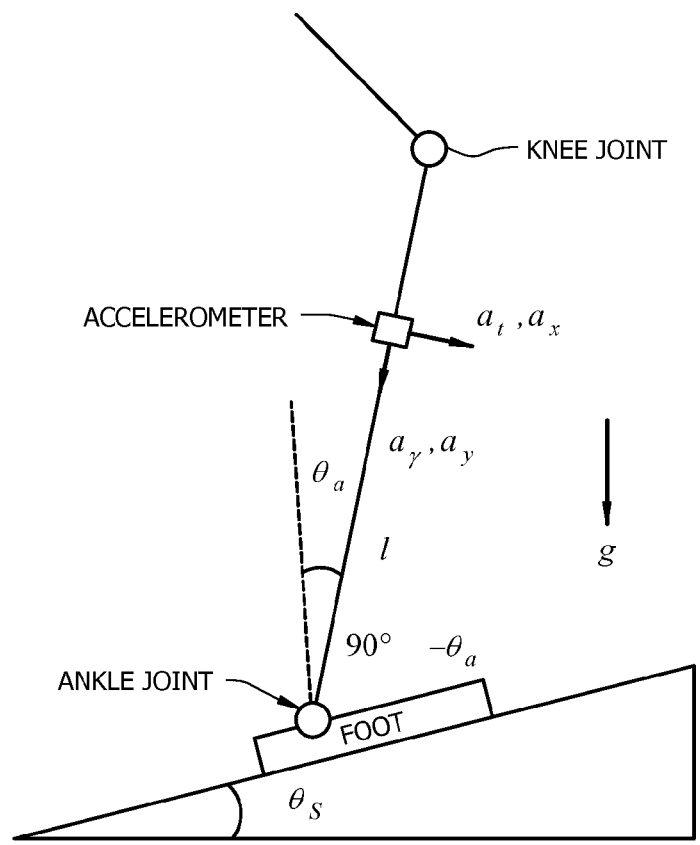
FIG. 24 is a schematic diagram of accelerometer measurements for slope estimation in accordance with an embodiment of the invention.

For example, in some embodiments, a 3D accelerometer capable of measuring ±3 g accelerations is embedded into the ankle joint coupler where the prosthetic foot is connected. An exemplary arrangement of such a system is shown by the schematic in FIG. 24. The accelerometer measurements are used to estimate the ground slope. In order to estimate the ground slope, the accelerometer data in tangential direction is used. Assuming the foot is flat on the ground, the ground slope angle, $\theta_s$, can be calculated as in equation (9) below.

$$\theta_s = \sin^{-1}\left(\frac{a_t}{g}\right) \quad (9)$$

Figure 25:
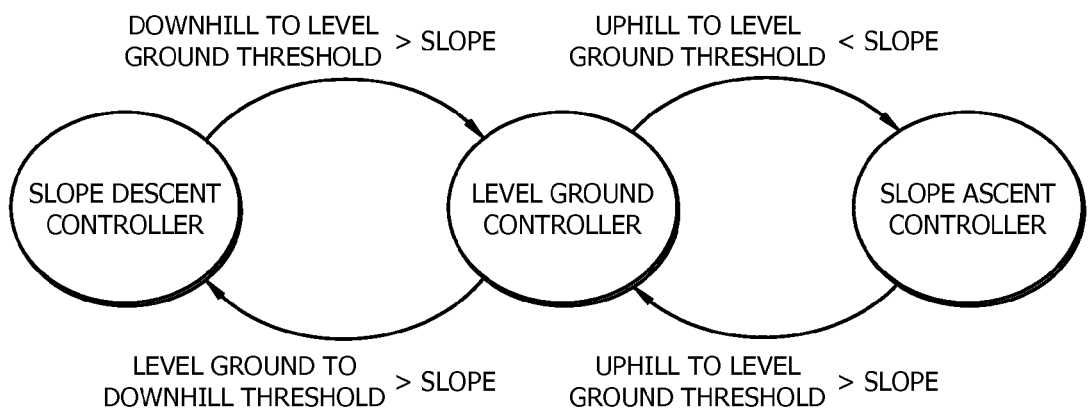
FIG. 25 is a state chart for slope estimation in a controller in accordance with an embodiment of the invention.

In Eqn. 9, g is the gravitational constant. In order to find the ground slope estimate, $\hat{\theta}_s$, the accelerometer data should be collected while the foot is flat on the ground as determined by the heel and ball of the foot load sensors. While the foot is flat on the ground, equation (1) is computed for the frame of the collected data and the mean of this frame is outputted as the ground slope estimate, $\hat{\theta}_s$. Once the slope is estimated, the intent recognizer selects the corresponding middle layer controller based on some predefined thresholds. An exemplary state chart for such an intent recognizer is shown in FIG. 25.

Friction and Cable Drive Based Actuation

Rather than a ballscrew and slider crank embodiment for the transmission of torque from a motor to the ankle and/or knee units, in some embodiments of the invention, the prosthesis can incorporate a friction and cable drive transmission embodiment. FIGS. 26A and 26B show front and back views of an exemplary embodiment of a friction drive transmission 2600 in accordance with an embodiment of the invention. As shown in FIGS. 26A and 26B, the shaft 2602 of an electric motor 2604 is preloaded against a first stage in a housing 2606, such as a larger diameter cylinder or friction drive gear 2608, which creates sufficient friction to transmit torque without slip. The shaft 2602 can use one or more friction rollers 2610 to transmit the torque. The first stage of the friction drive can also be supplemented with a second stage. The friction drive gear 2608 drives a smooth pinion 2612 directly, which is preloaded against a larger diameter cylinder or cable gear output 2614 in the housing 2606, which in turn transmits torque directly to the knee or ankle joint.

In addition to, or rather than a friction drive, the first or second stage of the transmission can alternatively be embodied by a cable drive transmission, in which a cable is wrapped around the circumference of a larger diameter cylinder, such as friction drive gear 2608, and also around the circumference of a smaller diameter cylinder, such as pinion 2612. In such embodiments, the cable is affixed to the friction drive gear 2608, and is pretensioned, using a tensioning screw 2616 or similar means, around both the drive gear 2608 and pinion 2612, such that friction between cable and pinion 2612 enables the transmission of torque from between the pinion 2612 and drive gear 2608. In one embodiment of a combined friction drive/cable drive transmission can be used, in which a first stage of the transmission (i.e., the friction drive gear 2608 connected directly to the electric motor 2604) is of the friction drive type, while the second stage of the transmission (i.e., the cable gear output 2614 connected directly to the knee or ankle joint) is of the cable drive type.

Applicants present certain theoretical aspects above that are believed to be accurate that appear to explain observations made regarding embodiments of the invention. However, embodiments of the invention may be practiced without the theoretical aspects presented. Moreover, the theoretical aspects are presented with the understanding that Applicants do not seek to be bound by the theory presented.

While various embodiments of the invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the invention should not be limited by any of the above described embodiments. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this invention belongs. It is further understood that terms, such as those defined in commonly used dictionaries, should be interpreted as having a meaning that is consistent with their meaning in the context of the relevant art and will not be interpreted in an idealized or overly formal sense unless expressly so defined herein.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the following claims.

What is claimed is:

1. A powered leg prosthesis, comprising:
    a powered knee joint comprising a knee joint and a knee motor unit for delivering power to said knee joint;
    a powered ankle joint coupled to said knee joint comprising an ankle joint and an ankle motor unit to deliver power to said ankle joint;
    a prosthetic foot coupled to said ankle joint;
    a plurality of sensors for measuring a real-time input; and
    a control system communicatively coupled to said powered knee joint, said powered ankle joint, and said plurality of sensors and configured for concerting operation of said powered knee joint and said powered ankle joint based on said real-time input via control signals, the control system comprising:
        a processor, and
        a memory storing instructions for causing the processor to perform steps comprising:
            for each of the powered knee joint and the powered ankle joint, performing a torque decomposition based on the real-time input to obtain a passive portion of a joint torque and an active portion of the joint torque, and
            generating control signals for each of the powered knee joint and the powered ankle joint based at least on the real-time input, the passive portion of the joint torque, and the active portion of the joint torque.

2. The leg prosthesis of claim 1, the plurality of sensors further comprising at least one position sensor located at said knee joint and at least one position sensor at said ankle joint.

3. The leg prosthesis of claim 1, further comprising an assembly coupled to said knee joint that includes a motor connected to a ballscrew.

4. The leg prosthesis of claim 1, wherein at least one of the knee motor unit and the ankle motor unit deliver power using at least one among a cable drive or a friction drive.

5. The leg prosthesis of claim 1, further comprising an assembly coupled to said ankle joint that includes a motor connected to a ballscrew in parallel with a spring, said spring increasing peak torque and power capability of said ankle joint.

6. The leg prosthesis of claim 1, wherein said foot further comprises a ball and a heel.

7. The leg prosthesis of claim 6, wherein at least a portion of the plurality of sensors measure a sagittal plane moment and ground interaction forces at said ball and at said heel.

8. The leg prosthesis of claim 1, wherein said active portion results from an interaction between a user and said prosthesis measured by said plurality of sensors, and wherein said passive portion has a spring-dashpot behavior.

9. The leg prosthesis of claim 1, wherein the instructions for performing the torque decomposition further comprises instructions for solving a constrained optimization problem.

10. The leg prosthesis of claim 1, wherein the plurality of sensors further comprises at least one accelerometer for measuring shank accelerations in the frontal, sagittal, and axial planes and at least one accelerometer for measuring foot accelerations in the frontal, sagittal, and axial planes.

11. The leg prosthesis of claim 1, wherein said memory is further configured for storing instructions for controlling causing the processor to perform a step comprising: recognizing an intent of a user of said prosthesis via signals from said plurality of sensors and configuring the control signals to provide a current gait based on the recognized intent.

12. The leg prosthesis of claim 11, wherein said memory is further configured for storing instructions for causing the processor to perform a step comprising: based on said recognized intent of said user, modulating the control signals to smooth transition behavior within the current gait or between a previous gait and the current gait.

13. The leg prosthesis of claim 11, wherein the instructions for performing said recognizing of said intent further comprises instructions for determining an activity mode of said prosthesis including at least one of standing, walking, ascending, descending, and sitting by comparing stored (recent) samples from said plurality of sensors to a stored sample database.

14. The leg prosthesis of claim 11, wherein the instructions for performing said recognizing of said intent further comprises instructions for estimating a cadence of the user based on the intervals of the ground reaction peaks from said sensor between consecutive strides.

15. The leg prosthesis of claim 14, wherein the instructions for said generating of said control signals further comprises instructions for modulating the control signals based on said estimated cadence.

16. The leg prosthesis of claim 11, where said memory is further configured for storing instructions for causing the processor to perform a step comprising: estimating a ground slope based on an accelerometer placed below the ankle joint for measuring foot accelerations in the frontal, sagittal, and axial planes.

17. The leg prosthesis of claim 16, wherein the instructions for said generating of said control signals further comprises instructions for modulating the control signals based on said estimated ground slope.

18. The leg prosthesis of claim 1, wherein the computer readable medium memory is further configured for storing instructions for causing the processor to perform a step comprising: determining a sitting phase of a user during a sitting mode.

19. The leg prosthesis of claim 18, wherein the instructions for said generating of said control signals further comprises instructions for varying a power delivered to at least one of said ankle joint or said knee joint according to said sitting phase.

20. A powered leg prosthesis, comprising:
    a powered knee joint comprising a knee joint and a knee motor unit for delivering power to said knee joint;
    a prosthetic lower leg having a socket connector above said knee joint;
    a powered ankle joint coupled to said lower leg opposite said knee joint comprising an ankle joint and an ankle motor unit to deliver power to said ankle joint;
    a prosthetic foot including a ball and a heel;

a plurality of sensors for providing a sagittal plane moment, and ground interaction forces at said ball and at said heel, and a control system communicatively coupled to said powered knee joint, said powered ankle joint, and said plurality of sensors for extracting real-time input from said user based on data from said plurality of sensors and for concerting operation of said powered knee joint and said powered ankle joint based on said real-time input via control signals, the control system comprising:

a processor, and a memory storing instructions for causing the processor to perform steps comprising:

for each of the powered knee joint and the powered ankle joint, performing a torque decomposition based on the real-time input to obtain a passive portion of a joint torque and an active portion of the joint torque, and generating the control signals, the control signals configured for adjusting a torque at each of the powered knee joint and the powered ankle joint based at least on the real-time input, the passive portion of the joint torque, and the active portion of the joint torque.

21. The leg prosthesis of claim 20, wherein at least one of the knee motor unit and the ankle motor unit deliver power using at least one among a cable drive or a friction drive.

22. A powered leg prosthesis, comprising:

a powered knee joint comprising a knee joint and a knee motor unit for delivering power to said knee joint;

a powered ankle joint coupled to said knee joint comprising an ankle joint and an ankle motor unit to deliver power to said ankle joint;

a prosthetic foot coupled to said ankle joint;

a plurality of sensors for measuring a real-time input, the real-time input comprising interaction forces, joint angles, and angular velocities; and a control system communicatively coupled to said powered ankle joint, said powered knee joint and said plurality of sensor and configured for inferring an intent of a user based on said real-time input and concerting operation of said powered knee joint and said powered ankle joint based on said inferred intent via at least torque control signals, the control system comprising:

a processor, and a memory storing instructions for causing the processor to perform steps comprising:

for each of the powered knee joint and the powered ankle joint, performing a torque decomposition based on the real-time input to obtain a passive portion of a joint torque and an active portion of the joint torque, and calculating torque control signals for adjusting a torque for each of the powered knee joint and the powered ankle joint based at least on the real-time input, the passive portion of the joint torque, and the active portion of the joint torque.

23. The powered leg prosthesis of claim 1, wherein said control system selectively operates said powered knee joint and said powered ankle joint during a walking stride so that each of said powered knee joint and said powered ankle joint contributes torque for locomotion during said walking stride.

* * * * *